United States Patent
Sirianni et al.

(10) Patent No.: US 11,446,267 B2
(45) Date of Patent: Sep. 20, 2022

(54) NANOPARTICLE COMPOSITIONS, METHODS OF FABRICATION, AND USE FOR DRUG DELIVERY

(71) Applicant: DIGNITY HEALTH, Phoenix, AZ (US)

(72) Inventors: Rachael Sirianni, Sugar Land, TX (US); David Alexandro Medina, Phoenix, AZ (US); Eugene Chung, San Antonio, TX (US)

(73) Assignee: Dignity Health, Phoenix, AZ (US)

( * ) Notice: Subject to any disclaimer, the term of this patent is extended or adjusted under 35 U.S.C. 154(b) by 276 days.

(21) Appl. No.: 16/616,222

(22) PCT Filed: Jun. 15, 2018

(86) PCT No.: PCT/US2018/037934
§ 371 (c)(1),
(2) Date: Nov. 22, 2019

(87) PCT Pub. No.: WO2018/232366
PCT Pub. Date: Dec. 20, 2018

(65) Prior Publication Data
US 2020/0093769 A1    Mar. 26, 2020

Related U.S. Application Data

(60) Provisional application No. 62/520,228, filed on Jun. 15, 2017.

(51) Int. Cl.
*A61K 31/192* (2006.01)
*A61K 9/51* (2006.01)

(52) U.S. Cl.
CPC .......... *A61K 31/192* (2013.01); *A61K 9/5153* (2013.01)

(58) Field of Classification Search
CPC .................... A61K 31/192; A61K 9/5153
USPC ........................................ 514/570
See application file for complete search history.

(56) References Cited

U.S. PATENT DOCUMENTS 9,333,179 B2    5/2016    Zhang et al.
2011/0274759 A1    11/2011    Troiano et al.

FOREIGN PATENT DOCUMENTS

WO    2011/084513 A2    7/2011
WO    2014/028241 A1    2/2014

OTHER PUBLICATIONS

Maden, Malcolm, "Retinoid Signalling in the Development of the Central Nervous System", Nature Reviews Neuroscience, 3(11):843-853 (Nov. 2002).

Shalgunov, Vladimir et al., "Comprehensive study of the drug delivery properties of poly(L-lactide)-poly (ethylene glycol) nanoparticles in rats and tumor-bearing mice", Journal of Controlled Release, 261:31-42 (Jun. 10, 2017).

*Primary Examiner* — Kristin A Vajda
(74) *Attorney, Agent, or Firm* — Rodney J. Fuller; Booth Udall Fuller, PLC

(57) ABSTRACT

The invention relates to a composition and use of the composition in the treatment of a disorder, for example, a neurological disease associated with retinoid signaling. The invention also includes the use of a retinoid encapsulated in nanoparticles. The retinoid encapsulated nanoparticles are adapted to increasing lifespan and conferring neuroprotective effects such as preserving motor units, reducing motor impairment, or reducing neuroinflammation in a subject.

20 Claims, 13 Drawing Sheets

NANOPARTICLE COMPOSITIONS, METHODS OF FABRICATION, AND USE FOR DRUG DELIVERY

CROSS-REFERENCE TO RELATED APPLICATIONS

This application is the U.S. National Stage of International Application No. PCT/US2018/037934, filed on Jun. 15, 2018, which claims the benefit of U.S. Provisional Patent Application No. 62/520,228, filed on Jun. 15, 2017, the contents of each of which are incorporated herein by reference in their entireties.

STATEMENT REGARDING FEDERALLY SPONSORED RESEARCH

The present subject matter was made with government support under W81XWH-14-0311 awarded by the Department of Defense. The government has certain rights in the present subject matter.

TECHNICAL FIELD

The disclosure relates to a pharmaceutical composition, use, and composition, and more particularly to such pharmaceutical composition, use, and composition employing nanoparticles in the treatment of diseases.

BACKGROUND

All publications cited herein are incorporated by reference in their entirety to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Neurodegenerative diseases affect millions of people worldwide. In the United States, more than five million people are living with Alzheimer's disease (AD), more than 500,000 people are living with Parkinson's disease (PD), and more than 20,000 people are living with Amyotrophic lateral sclerosis (ALS) at any given time. The diseases occur when nerve cells of the brain or peripheral nervous system lose function and die over time. Thus, the risk of being affected by a neurodegenerative disease increases with age.

The motor neuron diseases (MNDs) are progressive neurological disorders that destroy motor neurons. Motor neurons control essential voluntary muscle activity including breathing, speaking, swallowing, and walking. Messages from upper motor neurons (nerve cells in the brain) transmit to lower motor neurons (nerve cells in the brain stem or spinal cord) and in turn, to muscles. In MND, disruptions of the signals between the lowest motor neurons and the muscle cause improper function, gradual weakening, and uncontrollable twitching of the muscles. Disruptions of the signals between the upper and the lower motor neurons cause the stiffness of limb muscles, slow and effortful movements, overactive tendon reflexes, and loss of the ability to control voluntary movement.

ALS is a progressive neurodegenerative disorder that ultimately leads to death. The average age at ALS onset is approximately 55 years. Clinical manifestations of ALS involve both upper motor neurons (enhanced and pathological reflexes and spasticity) and lower motor neurons (focal and multifocal muscle weakness and atrophy, fasciculations and cramps) [1]. Over 90% of ALS cases are idiopathic. A variety of processes are known to contribute to disease progression, e.g., oxidative stress, mitochondrial dysfunction, abnormal axonal transport, and protein aggregation, with cellular toxicity and inflammation producing progressive death of motor neurons [2, 3]. In the US, the prevalence of ALS is 4-6 cases per 100,000, with an average of 15 people being diagnosed every day. Current treatments offer, on average, a 5-year survival prognosis. There is a lack of new therapeutics. Only two drugs have obtained FDA approval for ALS in the last 20 years. Riluzole, received FDA approval in 1995, modestly delays symptom onset and extends survival by 2-3 months. Edaravone, received FDA approval in 2017, was shown to reduce disease progression in a subset of ALS patients in a phase III study of 137 patients [4]. Thus, there is an unmet need to advance new therapies for the treatment of neurologic disorders such as ALS.

An obstacle to developing therapeutics for neurological diseases is delivery to the brain and the spinal cord. Tight junctions between endothelial cells form the blood-brain barrier (BBB) and blood-spinal cord barrier (BSCB), which are passive barriers to diffusion. Efflux carriers, such as the P-glycoprotein pump (PGP), also actively transport therapeutics out of cells and back into systemic circulation [5-7]. In general, drugs that are capable of reaching the brain and spinal cord are lipophilic, which facilitates diffusion through cellular membranes [8]. Hydrophobic drugs suffer from additional barriers to delivery which include poor solubility and inefficient tissue penetration, preventing them from being effectively utilized in the clinic [9]. For example, highly hydrophobic drugs such as Adapalene (with less than 1 μg/ml solubility in water) is rapidly cleared from the plasma. Even if adapalene is maximally solubilized, no more than 0.24 μg per week can be delivered subcutaneously using a 2-ml ALZET mini pump. Acute infusion directly into the brain, although possible, is highly invasive and difficult to implement long term. Thus, there is also an unmet need to deliver new therapies for the treatment of neurologic disorders such as ALS.

BRIEF SUMMARY OF THE INVENTION

The present invention is directed to therapeutic nanoparticles and uses thereof to treat a disorder. In one embodiment, the therapeutic nanoparticles comprise a poly(lactic) acid-poly(ethylene)glycol (PLA-PEG) copolymer comprising PLA having a number-average molecular weight of 9-23 kg/mole, and PEG having a number-average molecular weight of 0.5-10 kg/mole; a polymer, wherein the polymer is a short-chain polyester having a number-average molecular weight of 0.5-8 kg/mole; and a biologically active ingredient.

In another embodiment, the therapeutic nanoparticles comprise a polymer having a number-average molecular weight of 20-70 kg/mole, an amphiphilic lipid having a number-average molecular weight of 0.3-0.8 kg/mole; and a biologically active ingredient. Non-limiting example of a amphiphilic lipid, include amphiphilic lipids include lecithin, distearoylphosphatidylethanolamine (DSPE), cholesterol, 1,2-dipalmitoyl-sn-glycero-3-phosphocholine (DPPC), rhamnolipid, phospholipids, dioleoyltrimethyl-ammoniumpropane (DOTAP), a pegylated lipid, and combinations thereof.

Non-limiting examples of polymers include polycaprolactone (PCL), PLA, poly(lactic-co-glycolic acid) (PLGA), poly (glycolic-acid) (PGA), poly (lactide-co-caprolactone), polyethylene adipate, polybutylene succinate, polyhydroxybutyrate, polyhydroxyalkanoate, poly(3-hydroxybutyrate-co-3-hydroxyvalerate), and combinations thereof.

In particular embodiments, the PLA-PEG has a weight average molecular weight of 10 to 40 kg/mol and/or the weight percent of PLA-PEG is between 50 to 94.8, and the weight percent of the short-chain polyester is between 5 to 49.8.

In certain embodiments, the active ingredient has a partition coefficient (log P) of 2-10 and/or the weight percent of the active ingredient is between 0.2 to 5 of the total weight percent of the nanoparticle. In one specific example, the active ingredients includes a retinoid, more specifically, adapalene, retinoic acid, BMS 753, AM 80, EC19, CD1530, AM 580, TTNB, Ch 55, BS 961, AC 55649, AC261066, BMS 543, EC 23, Fenretinide, Isotretinoin, and Tazarotene.

In one embodiment, 5-90% of the active ingredient, or in a more specific embodiment, 10-40%, is released from the therapeutic nanoparticles over 24 hours when placed in a phosphate buffer solution at room temperature.

The invention is also directed to a method of treating a subject having a disorder, for example, a disorder associated with retinoid signaling in the central nervous system (CNS). The method typically comprises administering to the subject a therapeutically effective amount of a nanoparticle of the invention. In specific embodiments, the nanoparticles are used in the manufacture of a medicament for the treatment of a disorder. The method may be used to treat many disorders, for example: a central nervous system disorder, neuromuscular degeneration in the periphery, cancer, a non-neurodegenerative-CNS disease, a motor neuron disease (e.g, amyotrophic lateral sclerosis (ALS), progressive bulbar palsy, pseudobulbar palsy, primary lateral sclerosis (PLS), progressive muscular atrophy, spinal muscular atrophy (SMA), and post-polio syndrome (PPS)), a neurodegenerative disease (e.g, ALS, Parkinson's disease (PD), Alzheimer's disease (AD), Huntington's disease (HD), motor neuron disease, Schizophrenia), a neurotrauma, a neurodevelopmental disease, a neuropsychiatric illness, and stroke. The neurotrauma include a traumatic brain injury (TBI), and the neurodevelopmental disease comprises spinocerebellar ataxia. The treatment method may increase the lifespan, reduce motor impairment, reduce loss of motor neuron, reduce loss of neuromuscular junction (NMJ) innervation, reduce loss of muscle volume, or reduce expression of a neuroinflammation marker, such as, phosphorylated neurofilament heavy chain, glial fibrillary acidic protein, and Iba-1.

In one particular embodiment, the therapeutic nanoparticle is administered systemically, e.g., parenterally, such as, intravenously, direct injection into the brain, injection into the intrathecal space of the spinal cord, injection into the CSF of the subarachnoid space of the brain or cerebral ventricles, intranasal injection, subcutaneous injection, or intramuscular injection.

In yet another embodiment, the invention is directed to a method of fabricating a therapeutic nanoparticle. For example, in a specific example, the method includes the steps of forming an organic phase, wherein the organic phase comprises an organic solvent, PLA-PEG comprising PLA having a number-average molecular weight of 9-23 kg/mole and PEG having a number-average molecular weight of 0.5-10 kg/mole, a polymer having a number-average molecular weight of 0.5-8 kg/mole, and a biologically active ingredient. The method may further include combining the organic phase with a first aqueous phase to form a pre-emulsion mixture; emulsifying the pre-emulsion mixture to form an emulsion; combining the emulsion with a second aqueous phase; and evaporating the organic solvent from the combination of the emulsion and the second aqueous solution.

In a varying embodiment, the method of fabricating a therapeutic nanoparticle comprises the steps of forming an organic phase comprising an organic solvent, a polymer having a number-average molecular weight of 20-70 kg/mole, and a biologically active ingredient; forming an aqueous phase comprising an amphiphilic lipid having a number-average molecular weight of 0.3-0.8 kg/mole; combining the organic phase with the aqueous phase; and evaporating the organic solvent from the combination.

In certain specific embodiments, the therapeutic nanoparticles are fabricated between 0° C. and 8° C. The encapsulation efficiency in certain embodiment is between 60% and 95%.

Survival plot showing a significant delay in disease progression rate as calculated by time from disease onset (age at peak weight) to endpoint (Gehan-Breslow-Wilcoxon test, p=0.04). n per group: Ctl-NP=13; Adap-NP=23.

Figure 8:
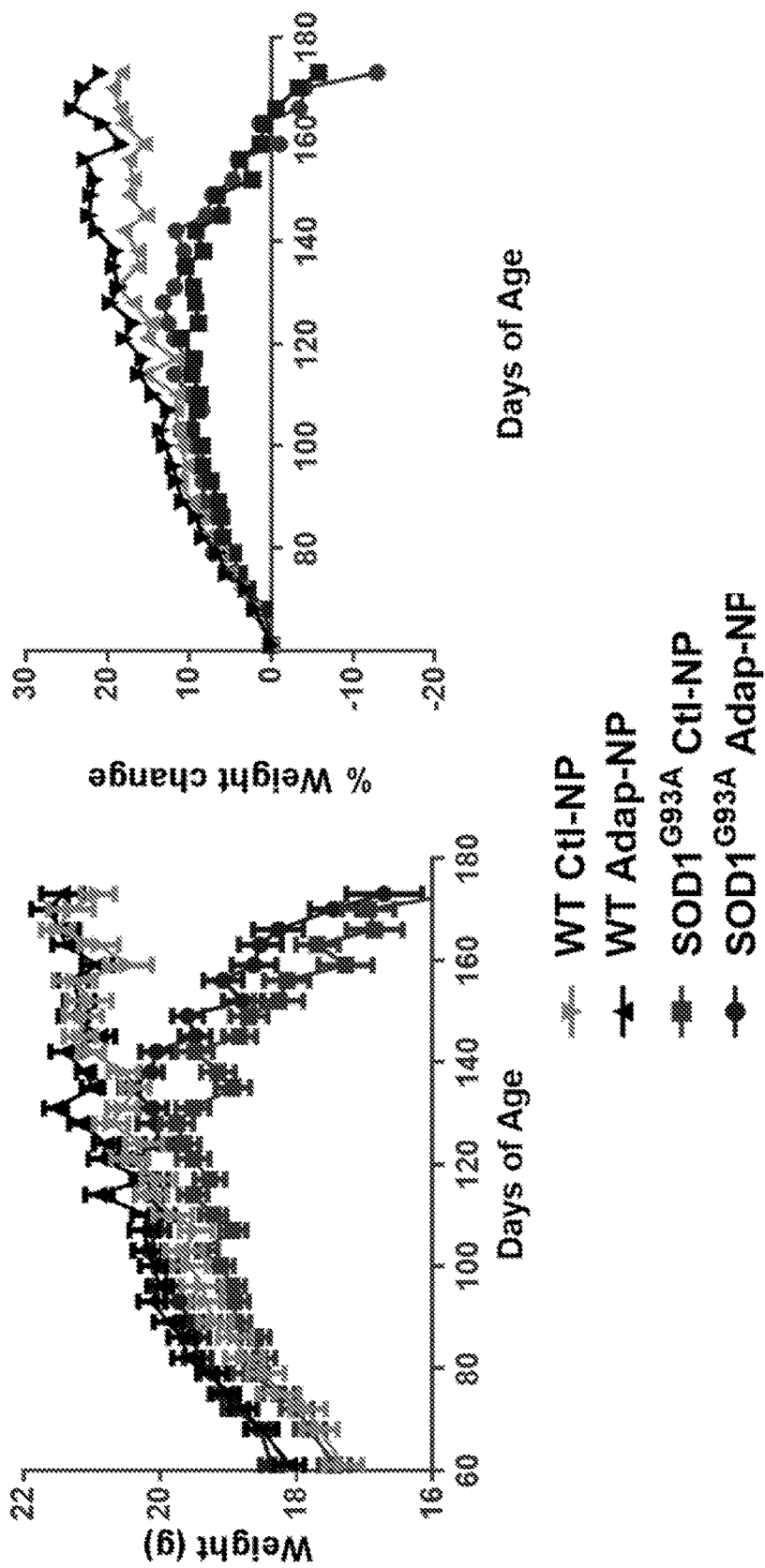

FIG. 8. Effects of Adap-NP on Weight in WT & SOD1$^{G93A}$ mice (A) Raw mouse weights beginning at day 60. (B) No significant differences in weight change were observed between SOD1$^{G93A}$ mice on Ctl-NPs and Adap-NPs.

Figure 9:
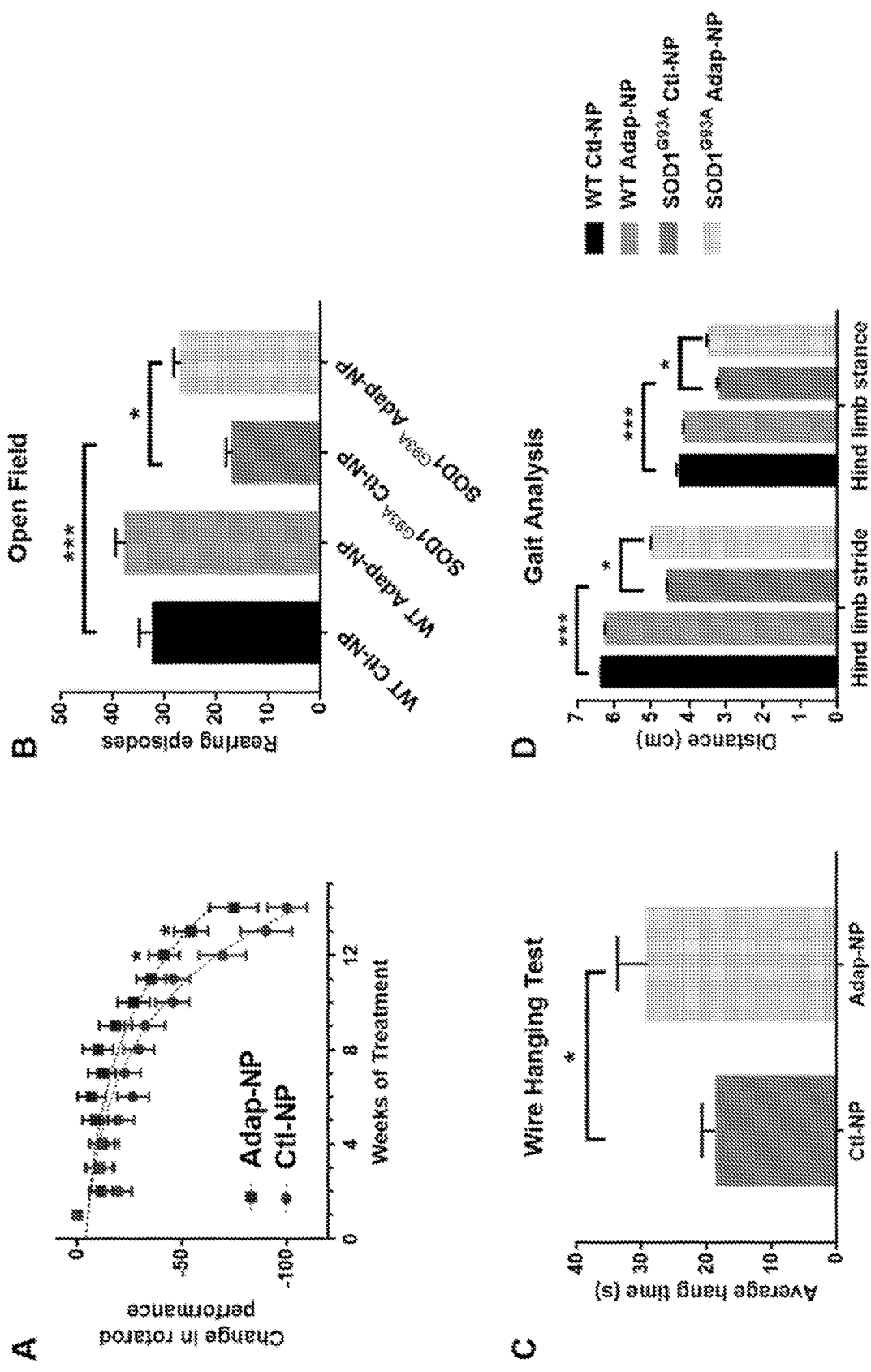

FIG. 9. Adap-NP administration significantly reduces motor impairments in SOD1$^{G93A}$ mice. (A) Normalized plot demonstrating a change in performance on the accelerating rotarod task (4-40 rpm for 300 secs) from baseline (average time from week 1). (B) The number of rearing episodes in an 8-minute open-field task. (C) Averaged wire hanging time of 3 trials. (D) Gait quantification from the foot-print assay. * represents p<0.05.

Figure 10:
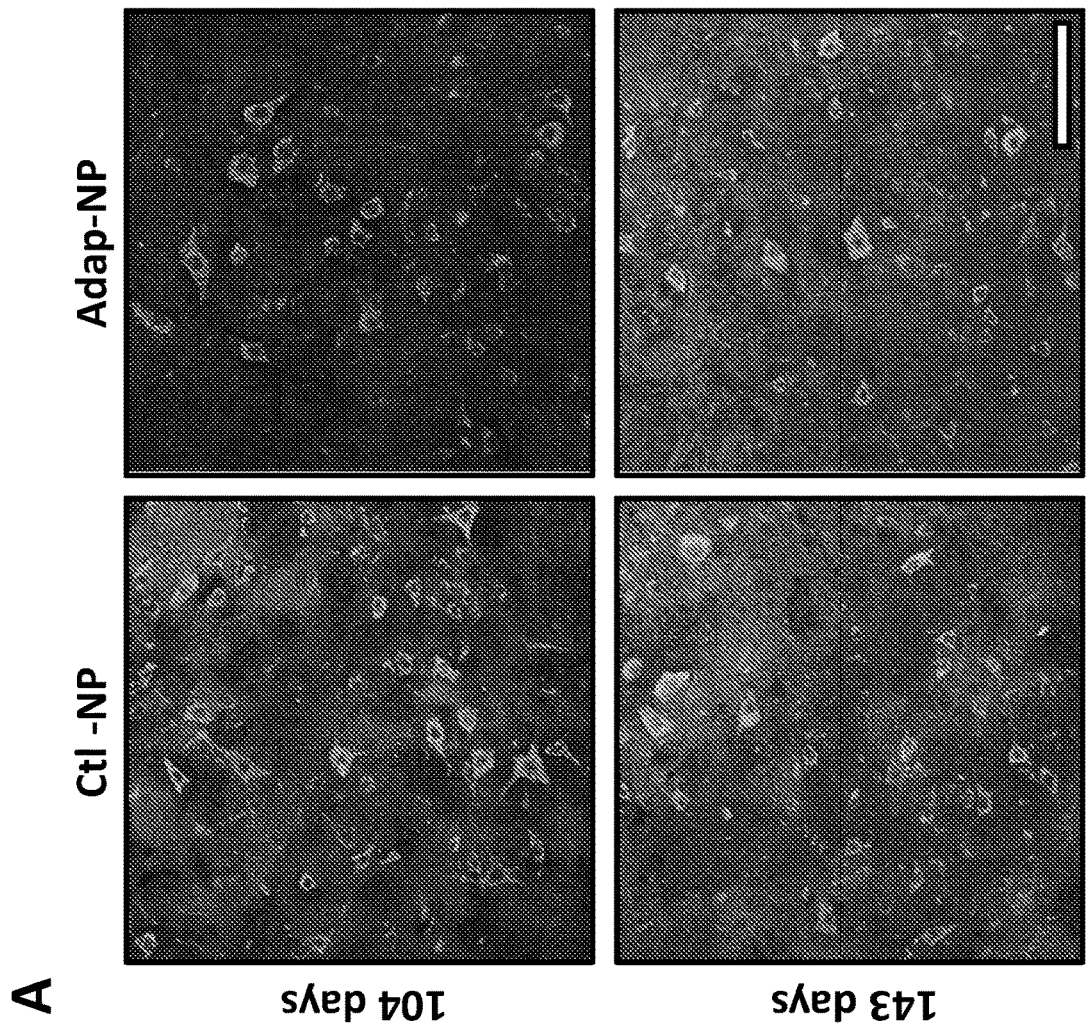
Figure 10:
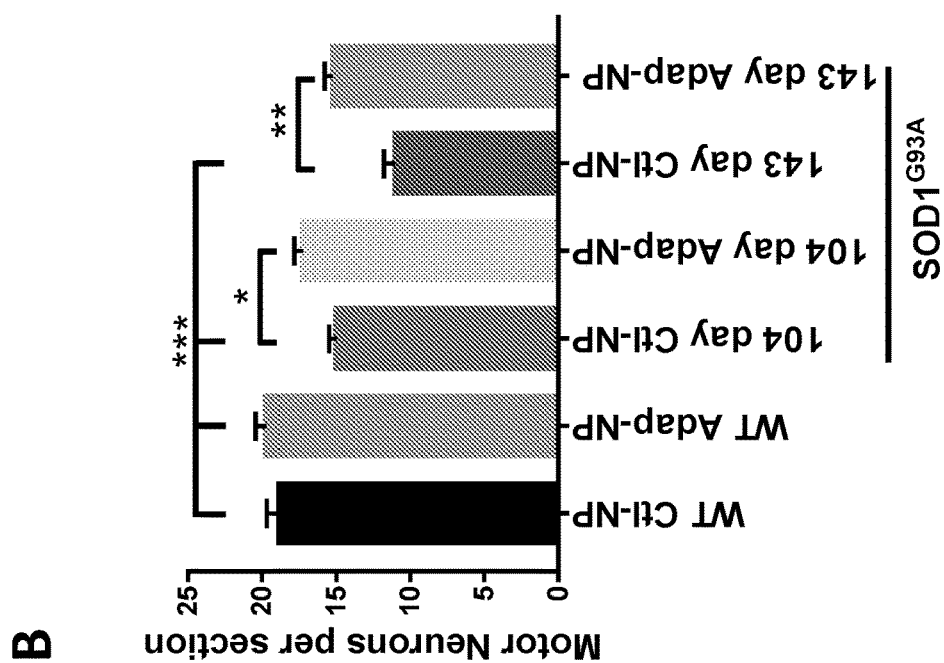

FIG. 10. Treatment with Adap-NPs significantly reduces neurodegeneration. (A) Immunofluorescence staining for ChAT (green) to identify motor neurons in the lumbar spinal cord at 143 days of age. (B) Quantification of motor neurons in lumbar spinal cord shows progressive loss of motor neurons in spinal cord is reduced with Adap-NP treatment (*=p<0.05, ***=p<0.001; two way ANOVA). n=12-20 sections per group.

Figure 11:
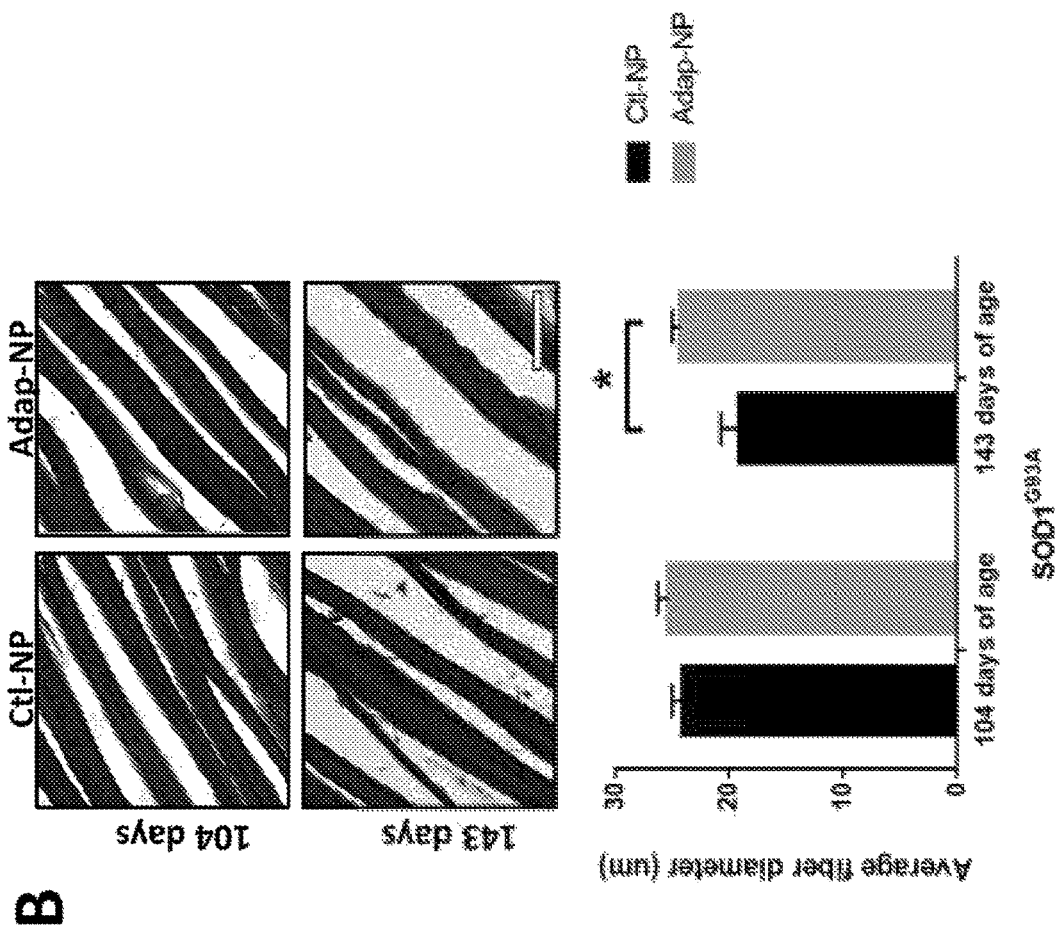
Figure 11:
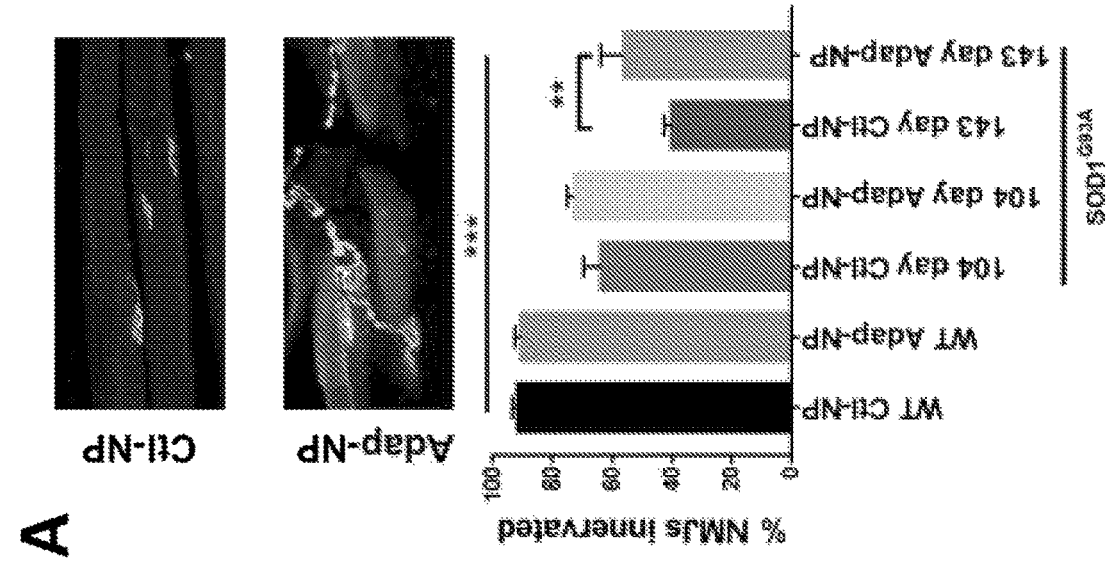

FIG. 11. Treatment with Adap-NPs reduces the degeneration of motor units in the SOD1G93A mice. (A) (Top) Immunofluorescence of neuromuscular junction (NMJ) using neurofilament (green) and bungarotoxin (red) (Bottom) Quantification of NMJ innervation demonstrates progressive loss of innervation in transgenic mice which is reduced with Adap-NP. (B) (Top) H&E stained muscle fibers from 104-day old (top row) and 143-day old (bottom row) transgenic mice. (Bottom) Quantification shows that Adap-NPs decrease muscle fiber atrophy compared to control. *=p<0.05, ***p<0.005, Student's t-test.

Figure 12:
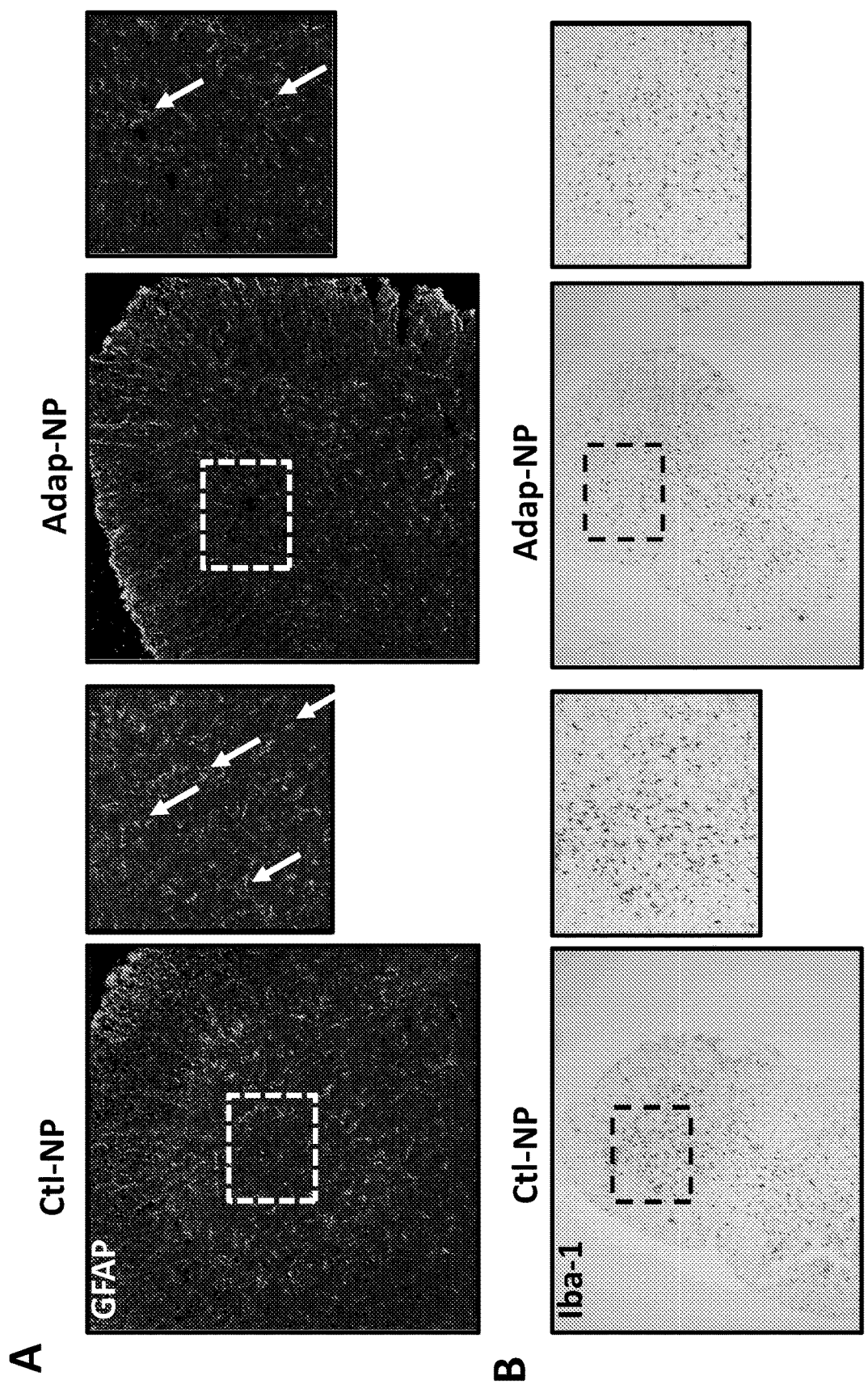

FIG. 12. Adap-NP administration reduces neuroinflammation markers in the spinal cords of SOD1$^{G93A}$ transgenic mice. (A) Immunofluorescence images of GFAP (green) taken from the ventral horn of the spinal cord from 143-day old SOD1$^{G93A}$ mice. White box marks where magnified images were acquired (on the right of lower mag images). (B) Immunofluorescence images of microglial marker Iba1 (green) taken from the ventral horn of the spinal cord from 143 day old SOD1$^{G93A}$ mice. White box marks where magnified images were acquired (on the right of lower mag images).

Figure 13:
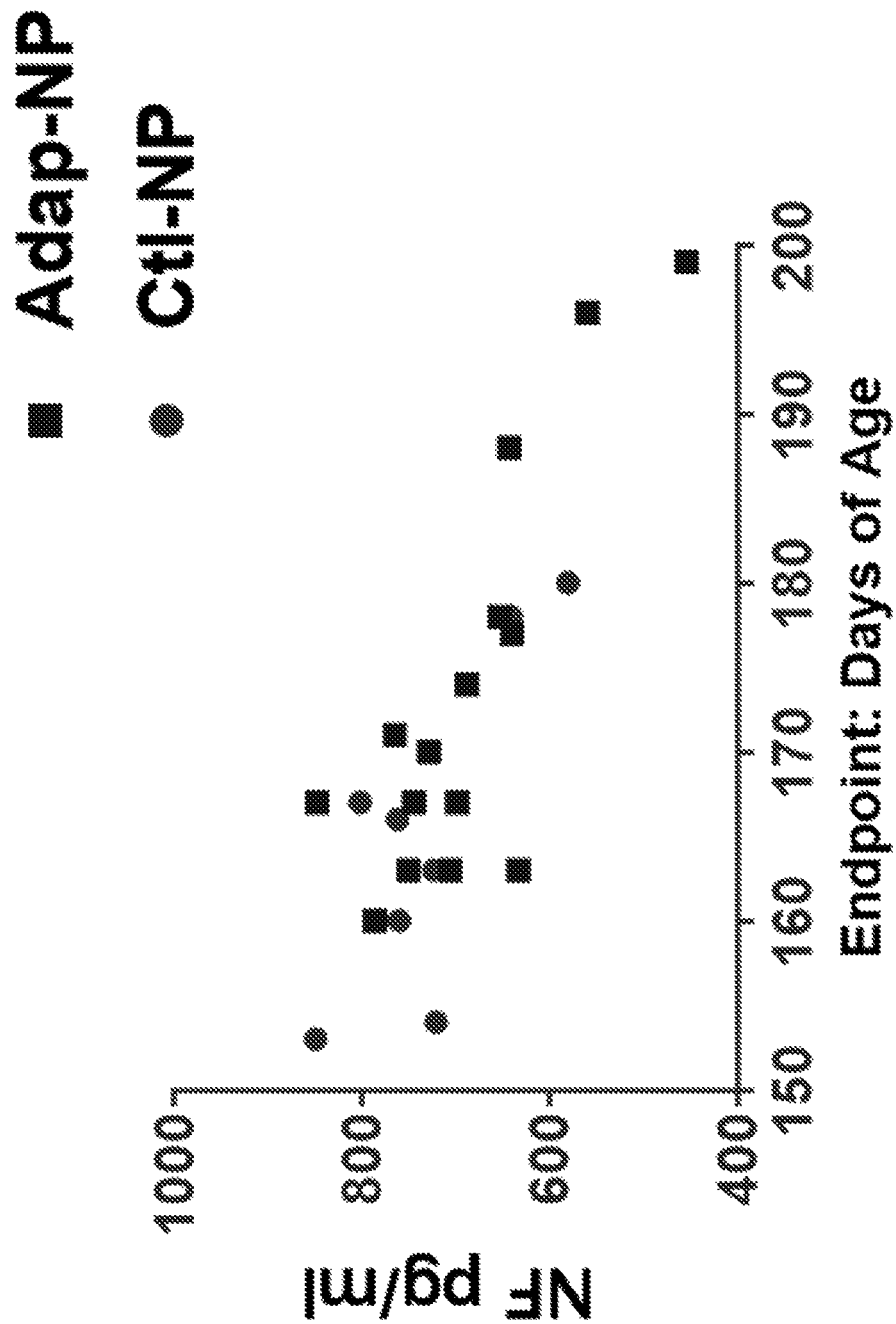

FIG. 13. Treatment with Adap-NPs was associated with significantly longer lifespan in SOD1$^{G93A}$ mice. Longer lifespan was also negatively correlated with decreased plasma levels phosphorylated neurofilament heavy chain.

DETAILED DESCRIPTION

As provided in greater detail herein, the disclosure provides drug delivery compositions, methods of fabrication, use of drug delivery compositions in the manufacture of a medicament, compositions for use in treatment, and methods of administration. The drug delivery composition or method disclosed herein at least partially rely on and incorporate one or more aspects of nanotechnology. In some embodiments, the drug delivery composition comprises a therapeutic nanoparticle. As used herein, the term "therapeutic nanoparticle" refers to therapeutics in nanoparticle systems having the potential to increase drug-loading capabilities, improve site-specific delivery, control release, sustain release, or a combination thereof. Therapeutics in nanoparticle systems have been shown to improve drugs pharmacokinetics through prolonged circulation, passive and/or, active accumulation in the target site, and prolonged release.

In particular embodiments herein, the invention is directed to nanoparticle formulations that enable encapsulation of therapeutically effective amount of a retinoid and treatment of disorders such as a central nervous system disorder, neuromuscular degeneration in the periphery, cancer, or a non-neurodegenerative-CNS disease in a subject. Additional objectives, advantages, and novel features will be set forth in the description which follows or will become apparent to those skilled in the art upon examination of the detailed description which follows.

Biologically Active Ingredient

As used herein, the term "water solubility" refers to the solubilities of the active ingredient in water, at a pressure of 1 atm and room temperature (approx. 293.15 K). In some embodiments, the active ingredient (e.g., a retinoid) has water solubility between 0.01 and 1 µM, or any number range in between, e.g., 0.02-1 µM, 0.02-0.8 µM, 0.04-0.8 µM, 0.04-0.6 µM, 0.05-0.6 µM, 0.05-1 µM or 0.05-0.5 µM. In other embodiments, the active ingredient (e.g., a retinoid) has a partition coefficient (log P) of between 2 and 10, or any number range in between, e.g., 3-10, 2-9.5, 3-9.5, 3-9, 4-9, 4-8.5, 4.5-8.5, 4.5-8, or 5-8. In yet other embodiments, the active ingredient, (e.g., a retinoid) has a partition coefficient (log P) of at least 2, at least 4, at least 6, at least 8, or at least 10.

In some aspects, the active ingredient comprises a highly hydrophobic retinoid. Non-limiting examples of highly hydrophobic retinoid include 4-[[(2,3-Dihydro-1,1,3,3-tetramethyl-2-oxo-1H-inden-5-yl)carbonyl]amino]benzoic acid (BMS 753), 3-[2-(5,6,7,8-Tetrahydro-5,5,8,8-tetramethyl-2-naphthalenyl)ethynyl]benzoic acid (EC19), 4-(6-Hydroxy-7-tricyclo[3.3.1.13,7]dec-1-yl-2-naphthalenyl) benzoic acid (CD1530), 3,7-Dimethyl-9-(2,6,6-trimethyl-1-cyclohexen-1-yl)-2E,4E,6E,8E, -nonatetraenoic acid (retinoic acid), 4'-Octyl-[1,1'-biphenyl]-4-carboxylic acid (AC 55649), 4-[(5,6,7,8-Tetrahydro-5,5,8,8-tetramethyl-2-naphthalenyl)carboxamido]benzoic acid (AM 580), 4-[(E)-2-(5,6,7,8-Tetrahydro-5,5,8,8-tetramethyl-2-naphthalenyl)-1-propenyl]benzoic acid (TTNB), 4-[[(5,6,7,8-Tetrahydro-5,5,8,8-tetramethyl-2-naphthalenyl)amino]carbonyl] benzoic acid (AM80), 4-[(1E)-3-[3,5-bis(1,1-Dimethylethyl)phenyl]-3-oxo-1-propenyl]benzoic acid (Ch 55), 4-[(1E)-2-(5,6-Dihydro-5,5-dimethyl-8-phenyl-2-naphthalenyl)ethenyl]-benzoic acid (BMS 543), 3-Fluoro-4-[[2-hydroxy-2-(5,5,8,8-tetramethyl-5,6, 7,8,-tetrahydro-2-naphthalenyl)acetyl]amino]-benzoic acid (BS 961), 4-[4-(2-Butoxyethoxy-)-5-methyl-2-thiazolyl]-2-fluorobenzoic acid (AC261066), 4-[2-(5,6,7,8-Tetrahydro-5,5,8,8-tetramethyl-2-naphthalenyl)ethynyl)-benzoic acid (EC 23), 6-[2-(3,4-Dihydro-4,4-dimethyl-2H-1-benzothiopyran-6-yl)ethynyl]-3-pyridinecarboxylic acid ethyl ester (Tazarotene), and N-(4-Hydroxyphenyl)retinamide (Fenretinide).

In other aspects, the retinoid comprises a RARβ-specific retinoid. Non-limiting examples of RARβ-specific retinoid include 3-[2-(5,6,7,8-Tetrahydro-5,5,8,8-tetramethyl-2-naphthalenyl)ethynyl]benzoic acid (EC19), 4-(6-Hydroxy-7-tricyclo[3.3.1.13,7]dec-1-yl-2-naphthalenyl)benzoic acid (CD1530), 3,7-Dimethyl-9-(2,6,6-trimethyl-1-cyclohexen-1-yl)-2E,4E,6E,8E,-nonatetraenoic acid (retinoic acid), 4-[(5,6,7,8-Tetrahydro-5,5,8,8-tetramethyl-2-naphthalenyl) carboxamido]benzoic acid (AM 580), 4-[(E)-2-(5,6,7,8-Tetrahydro-5,5,8,8-tetramethyl-2-naphthalenyl)-1-propenyl] benzoic acid (TTNB), 4-[(1E)-3-[3,5-bis(1,1-Dimethylethyl)phenyl]-3-oxo-1-propenyl]benzoic acid (Ch 55), 3-Fluoro-4-[[2-hydroxy-2-(5,5,8,8-tetramethyl-5,6,7,8,-tetrahydro-2-naphthalenyl)acetyl]amino]-benzoic acid (BS 961), 4'-Octyl-[1,1'-biphenyl]-4-carboxylic acid (AC 55649), 4-[4-(2-Butoxyethoxy-)-5-methyl-2-thiazolyl]-2-fluorobenzoic acid (AC261066), 4-[(1E)-2-(5,6-Dihydro-5,5-dimethyl-8-phenyl-2-naphthalenyl)ethenyl]-benzoic acid (BMS 543), 13-cis-Retinoic acid (Isotretoin), N-(4-Hydroxyphenyl)retinamide (Fenretinide), 4-[2-(5,6,7,8-Tetrahydro-5,5,8,8-tetramethyl-2-naphthalenyl)ethynyl]-benzoic acid (EC 23), and 6-[2-(3,4-Dihydro-4,4-dimethyl-2H-1-benzothiopyran-6-yl)ethynyl]-3-pyridinecarboxylic acid ethyl ester (Tazarotene). In yet other aspects, the retinoid comprises Adapalene. In further aspects, the retinoid is Adapalene.

"Encapsulation efficiency" of the active ingredient is calculated using:

$$\frac{\text{mass of active ingredient in } NPs}{\text{mass of active ingredient used in the formulation}} \times 100$$

In some embodiments, the encapsulation efficiency of the active ingredient (e.g., a retinoid) is between 50-100%, or any percent range in between, e.g., 55-100%, 55-90%, 60-95%, 60-90%, 65-95%, and 65-90%. In other embodiments, the encapsulation efficiency of the active ingredient (e.g., a retinoid) is at least 50%, at least 55%, at least 60%, at least 70% or at least 80%. In yet other embodiments, the encapsulation efficiency of the retinoid (e.g., Adapalene) is between 50-100%, 50-95%, or any percent range in between, e.g., 55-85%, 60-80%, 55-90%, or 60-80%. In further embodiments, the encapsulation efficiency of the retinoid (e.g., Adapalene) is at least 60%, at least 70%, at least 80%, or at least 90%.

"Content of the active ingredient" in the NPs (%, w/w) is calculated using:

$$\frac{\text{mass of active ingredient in } NPs}{\text{mass of } NPs \text{ recovered}} \times 100$$

In certain embodiments, the content of the active ingredient (e.g., a retinoid) in the NPs is, for example, at least 2%, at least 5%, at least 10%, at least 15%, or at least 20%. In other embodiments, the content of the active ingredient in the NPs is between 0.2% and 20%, e.g., 0.2-18%, 0.5-18%, 0.5-15%, 1-15%, 1-12%, 2-12%, 2-10%, 3-10%, 3-8%, 4-8%, 4-7%, or 5-7%. In yet other embodiments, the active ingredient is between 0.2% to 5% of the therapeutic NPs, or any % number in between, e.g., 0.2-4.5%, 0.4-4.5%, 0.4-4%, 0.6-4%, 0.6-3.5%, 0.8-3.5%, 0.8-3%, 1-3%, 1-2.5%, 1.2-2.5%, or 1.2-2%.

Polymer-Polyester Blend

In some embodiments, the therapeutic NPs include an amphiphilic polymer; a polymer having a number-average molecular weight of 0.5-8 kg/mole (a short-chain polyester); and an active ingredient. In other aspects, an amphiphilic copolymer is blended with a short-chain polyester.

Amphiphilic Polymer

Non-limiting examples of the amphiphilic copolymer include poly(lactic acid)-poly(ethylene glycol) (PLA-PEG), poly(lactic-co-glycolic acid)-poly(ethylene glycol) (PLGA-PEG), poly(lactic-co-glycolic acid)-d-α-tocopheryl polyethylene glycol succinate, poly(lactic-co-glycolic acid)-ethylene oxide fumarate, poly(glycolic acid)-poly(ethylene glycol), polycaprolactone-poly(ethylene glycol), any salts of the foregoing, and any derivatives of the foregoing. In some aspects, the amphiphilic polymer comprises PLA-PEG. In some embodiments, PLA-PEG comprises PLA having a number-average molecular weight (MW) of 9 to 23 kg/mole, e.g., 11-23, 11-21, 13-21, 13-19, 14-19, 14-18, 15-18, or 15-17 kg/mole. In other embodiments, PLA-PEG comprises PEG having a number-average MW of 0.5 to 10 kg/mole, e.g., 0.5-9, 1-9, 2-9, 2-8, 3-8, 3-7, 4-7, or 4-6 kg/mole. In other aspects, the ratio of PLA and PEG (PLA:PEG) is between 1:3 to 9:1, e.g., 1:3-8:1, 2:5-8:1, 2:5-7:1, 1:2-7:1, 1:2-6:1, 3:5-6:1, 3:5-5:1, 2:3-5:1, 2:3-4:1, 1:1-4:1, 1:1-3:1, or 1:1-2:1. In some aspects, PLA-PEG has a weight average molecular weight of between 10-40 kg/mole, e.g., 11-40, 11-38, 12-38, 12-36, 13-36, 13-34, 14-34, 14-32, 15-32, 15-30 or 18-25 kg/mole. In some embodiments, PLA-PEG is between 50% to 94.8% (weight percent) of the therapeutic NPs, e.g., 50-90%, 50-85%, 50-80%, 55-94.8%, 55-90%, 55-85%, 55-80%, 55-75%, 55-70%, or 55-65% c.

Hydrophobic Short-Chain Polyester

In some embodiments, the short-chain polyester having a number-average MW of 0.5 to 8 kg/mole, e.g., 0.5-7.5, 0.8-7.5, 0.8-7, 1.1-7, 1.1-6.5, 1.4-6.5, 1.4-6, 1.7-6, 1.7-5.5, 2-5.5, 2-5, 2.3-5, 2.3-4.5, 2.6-4.5, 2.6-4, or 3-4 kg/mole. Non-limiting examples of the hydrophobic short-chain polyester include, e.g., poly(3-hydroxybutyrate-co-3-hydroxyvalerate, polyethylene adipate, polybutylene succinate, polyhydroxybutyrate, polyhydroxyalkanoate, PCL, PLA, AND PLGA. In some aspects, the polyester is selected from the group consisting of PCL, PLA, and PLGA. In other aspects, the polyester comprises PCL. In yet other aspects, the polyester comprises PLGA. In some embodiments, the short-chain polyester, e.g., PCL, PLA, or PLGA is between 5% and 49.8% (wt percent) of the therapeutic NPs, e.g., 5-45%, 10-45%, 10-40%, 15-45%, 15-40%, 20-45%, 20-40%, 30-45%, or 30-40%.

Amphiphilic Polymer: Hydrophobic Short-Chain Polyester Weight Ratio

In some aspects, the ratio of the weight between the amphiphilic polymer and the hydrophobic short-chain polyester (e.g., PLA-PEG:PLGA) is between 1.1 and 19, e.g., 1.5-19, 1.5-18, 3-18, 3-15, 4.5-15, 4.5-14, 6-14, 6-12, 7.5-12, or 7.5-10.

Polymer-Lipid Hybrid

Polymer

Non-limiting examples of the polymer include, for example, poly(3-hydroxybutyrate-co-3-hydroxyvalerate, polyethylene adipate, polybutylene succinate, polyhydroxybutyrate, polyhydroxyalkanoate, PCL, PLA, AND PLGA. In some aspects, the polymer is selected from the group consisting of PCL, PLA, and PLGA. In other aspects, the polymer comprises PCL. In yet other aspects, the polymer comprises PLGA. In other aspects, the polymer has a number-average MW of 20 to 70 kg/mole, e.g., 22-70, 22-65, 25-65, 25-55, 28-55, 28-50, 30-50, 30-45, 32-45, or 32-42 kg/mole. In some embodiments, the polymer, e.g., PLGA is between 75% to 95.8% (weight percent) of the therapeutic NPs, e.g., 76-95%, 76-94%, 77-94%, 77-93%, 78-93%, 78-92%, 79-92%, 79-91%, 80-91%, or 80 to 89.8%.

Amphiphilic Lipid

Non-limiting examples of the amphiphilic lipid include lecithin, cholesterol, 1,2-dipalmitoyl-sn-glycero-3-phosphocholine (DPPC), dioleoyltrimethyl-ammoniumpropane (DOTAP), distearoylphosphatidylethanolamine (DSPE), rhamnolipid, phospholipids, a pegylated lipid, such as DSPE-PEG, Cholesterol-PEG, DPPC-PEG, DOTAP-PEG, DSPE-PEG, rhamnolipid-PEG, or phospholipid-PEG, and combinations thereof.

In some embodiments, the amphiphilic lipid comprises lecithin having a number-average MW of 0.3 to 0.8 kg/mole, or any number range in between, e.g., 0.3-0.79, 0.4-0.79, 0.4-0.78, 0.5-0.78, 0.5-0.77, 0.6-0.77 or 0.6-0.76 kg/mole. In further embodiments, the amphiphilic lipid, e.g., lecithin, is between 4% to 24.8% (weight percent) of the therapeutic NPs, e.g., 5-24.8%, 5-24%, 6-24%, 6-23%, 7-23%, 8-23%, 8-22%, 9-22%, 9-21%, or 10-21%, 10-20%, or 10-19.8%.

In other embodiments, the amphiphilic lipid comprises DSPE-PEG. In some aspects, DSPE-PEG comprises DSPE having a number-average MW of 0.3 to 0.8 kg/mole, e.g., 0.3-0.79, 0.4-0.79, 0.4-0.78, 0.5-0.78, 0.5-0.77, 0.6-0.77 or 0.6-0.76 kg/mole. In other aspects, DSPE-PEG comprises PEG having a number-average MW of 1 to 5.1 kg/mole, e.g., 1-4.1, 1.3-4.1, 1.3-3.1, 1.6-3.1, 1.6-2.1, or 1.9-2.1 kg/mole. In further aspects, the pegylated lipid, e.g., DSPE-PEG, is between 4% to 24.8% (wt %) of the therapeutic NPs, e.g., 5-24.8%, 5-24%, 6-24%, 6-23%, 7-23%, 8-23%, 8-22%, 9-22%, 9-21%, or 10-21%, 10-20%, or 10-19.8%.

In some embodiments, the amphiphilic lipid comprises lecithin and DSPE-PEG. In other embodiments, the ratio between lecithin and DSPE-PEG is between 5% to 95% (wt %), e.g., 10-95%, 10-90%, 20-90%, 20-80%, 30-80%, 30-70%, 40-70%, 40-60%, or 45-55%. In some aspects, the ratio between lecithin and DSPE-PEG is 1:1, lecithin is between 2% to 22.8% (wt %) of the therapeutic NPs, e.g., 2-22%, 2.5-22%, 2.5-20%, 3-20%, 3-18%, 3.5-18%, 3.5-16%, 4-16%, or 5-14.8%; and DSPE-PEG is between 2% to 22.8% (wt %) of the therapeutic NPs, e.g., 2-22%, 2.5-22%, 2.5-20%, 3-20%, 3-18%, 3.5-18%, 3.5-16%, 4-16%, or 5-14.8%.

Polymer: Amphiphilic Lipid Weight Ratio

In some aspects, the ratio of the weight between the polymer and the amphiphilic lipid (e.g., PLGA:lecithin/DSPE-PEG) is between 3.3 and 24, or any number in between, e.g., 3.5-22, 4-22, 4-21, 4.5-21, 4.5-20, 5-20, 5.5-20, or 5.5-18.

The Therapeutic NPs

In some embodiments, the hydrodynamic diameter of the therapeutic NPs (e.g., PLA-PEG/hydrophobic short-chain polyester NPs loaded with a retinoid such as Adapalene, or lipid-hybrid NPs loaded with a retinoid such as Adapalene) is 50 to 300 nm, or any number range in between, e.g., 50-265, 55-265, 55-230, 60-230, 60-200, 65-200, 65-180, 70-180, 70-160, 75-160, 75-130, or 80 to 130 nm.

In other embodiments, the zeta potential of the therapeutic NPs (e.g., PLA-PEG/hydrophobic short-chain polyester NPs loaded with a retinoid such as Adapalene, or lipid-hybrid NPs loaded with a retinoid such as Adapalene) is −50 to +20 mV, or any number range in between, e.g., −50 to +15, −50 to +10, −45 to +20, −45 to +15, −45 and +10, −40 to +20, −40 to +15, or −40 to +10 mV. In yet other embodiments, the zeta potential of the therapeutic NPs is −35 to +5 mV, or any number range in between, e.g., −35 to 0, −30 to 0, −30 to −5, −25 to −5, −25 and −10, or −20 to −10 mV.

In some aspects, the therapeutic NPs (e.g., PLA-PEG/hydrophobic short-chain polyester NPs loaded with a retinoid such as Adapalene, or lipid-hybrid NPs loaded with a retinoid such as Adapalene) release 5-40% of the active ingredient over 24 hours when placed in a phosphate buffer solution at room temperature, or any percentage range in between, e.g., 5-35%, 10-35%, 10-30%, 15-30%, 15-25%, or 20-30%. In other embodiments, the therapeutic NPs release 10-90% of the active ingredient over 24 hours when placed in a phosphate buffer solution at room temperature, or any percentage range in between, e.g., 10-85%, 12-85%, 12-80%, 15-80%, 15-75%, 18-75%, 18-70%, 20-70%, 20-60%, 25-60%, 25-50%, or 30-50%.

NP Fabrication Using Emulsion-Evaporation

Organic Solvent

In some aspects, the therapeutic NP is fabricated using an emulsion-evaporation method. In some embodiments, the organic solvent is selected from the group consisting of dichloromethane (DCM), ethyl acetate, benzyl alcohol, dimethyl sulfoxide, acetonitrile, chloroform, toluene, methyl ethyl ketone, acetone, acetic acid, and dimethylformamide. In other embodiments, the organic solvent comprises DCM.

Pre-Emulsion Aqueous Phase

Some embodiments of the disclosure comprise combining the organic phase with a pre-emulsion aqueous phase to form a pre-emulsion mixture. In certain non-limiting embodiments, the pre-emulsion aqueous phase comprises one or more hydrophilic solvents (e.g., water). In some aspects, the aqueous phase comprises a surfactant. As used herein, the term "surfactant" refers to any substance that tends to reduce the surface tension between two different molecules. In some aspects, surfactant tends to reduce the surface tension between two liquids. In other aspects, surfactant tends to reduce the surface tension between a liquid and a solid (e.g., the aqueous phase and the active ingredient). In some embodiments, the first aqueous phase comprises a surfactant selected from the group consisting of: sodium cholate, poly(vinyl alcohol), didodecyldimethylammonium bromide (DMAB), Pluronic, vitamin E TPGS, and TWEEN. In other embodiments, the second aqueous phase comprises a surfactant selected from the group consisting of: sodium cholate, poly(vinyl alcohol), didodecyl dimethylammoniumbromide (DMAB), Pluronic F68, vitamin E TPGS, and TWEEN. Some aspects of the disclosure include dissolving the surfactant in the aqueous phase using a physical force (e.g., mixing, vortexing, or shaking). Other aspects of the disclosure require no significant or material physical force for dissolving the surfactant in the aqueous phase. In some aspects, the surfactant acts as an emulsifier to provide for a mixing of the organic phase and the aqueous phase. In other aspects, the aqueous phase comprises a stabilizer. As used herein, the term "stabilizer" refers to any substance capable of inhibiting the separation of the organic phase and the aqueous phase. In some embodiments, the first aqueous phase comprises a stabilizing agent selected from the group consisting of: sodium cholate, poly(vinyl alcohol), didodecyldimethylammonium bromide (DMAB), Pluronic F68, vitamin E TPGS, and TWEEN. In other embodiments, the second aqueous phase comprises a stabilizing agent selected from the group consisting of: sodium cholate, poly(vinyl alcohol), didodecyldimethylammonium bromide (DMAB), Pluronic F68, vitamin E TPGS, and TWEEN. Some aspects of the disclosure include dissolving the stabilizing agent in the aqueous phase using a physical force (e.g., mixing, vortexing, or shaking). Other aspects of the disclosure require no significant or material physical force for dissolving the stabilizing agent in the aqueous phase. In some aspects, the stabilizing agent acts as an emulsifier to provide for a mixing of the organic phase and the aqueous phase. In some embodiments, the first aqueous phase comprises 0.5-5% (w/v) sodium cholate, or any number range in between, e.g., 0.5-4%, 0.6-4%, 0.6-3%, 0.7-3%, 0.7-2%, 0.8-2%, 0.8-1.5%, 0.9-1.5%, or about 1% (e.g., 0.9-1.1%). In other embodiments, the second aqueous phase comprises 0.1-1.5% (w/v) sodium cholate, or any number range in between, e.g., 0.1-1.3%, 0.12-1.3%, 0.12-1.1%, 0.14-1.1%, 0.14-0.9%, 0.16-0.9%, 0.16-0.7%, 0.18-0.7%, 0.19-0.5%, 0.2-0.4%, or about 0.3% (e.g., 0.25-0.35%).

Mixing the Organic Phase with the Aqueous Phase

The method of fabricating the therapeutic NPs comprises mixing an organic phase with an aqueous phase. In some aspects, a physical force (e.g., mixing, vortexing, or shaking) is applied to the polymer-organic solvent mixture to dissolve the polymer in the organic solvent. In other aspects, the amphiphilic polymer will go into solution without the addition of any significant or material physical force.

Removal of Organic Solvent

In some aspects, after removal of the organic solvent (e.g., by evaporation) and formation, the drug delivery composition is collected and washed. For example, after evaporation, the resulting mixture is filtered through a filter of desirable size (e.g., 0.22 μM) and the resulting filtrate is filtered again using filter tubes (e.g., 100 kiloDalton cut-off) and centrifugation methodologies.

In some aspects, dissolved polymer and the bioactive ingredient (e.g., Adapalene) are added dropwise into the first aqueous solution (e.g., 1% sodium cholate) with rapidly vortexing. In other aspects, the mixture of the polymer, bioactive ingredient, and aqueous solution are further probe sonicated. In yet other aspects, the resulting emulsion is dispersed in a second aqueous solution (e.g., 0.3% sodium cholate) and gently stirred to evaporate the solvent. In further aspects, following solvent evaporation, the solution is washed and concentrated. In some embodiments, washing and concentrating the NPs uses centrifugal filtration, e.g., an Amicon Ultra-15 Centrifugal filter. In other embodiments, washing and concentrating the NPs uses tangential flow filtration.

Amphiphilic Polymer

Non-limiting examples of the amphiphilic copolymer include poly(lactic acid)-poly(ethylene glycol) (PLA-PEG), poly(lactic-co-glycolic acid)-poly(ethylene glycol) (PLGA-PEG), poly(lactic-co-glycolic acid)-d-α-tocopheryl polyethylene glycol succinate, poly(lactic-co-glycolic acid)-ethylene oxide fumarate, poly(glycolic acid)-poly(ethylene glycol), polycaprolactone-poly(ethylene glycol), any salts of the foregoing, and any derivatives of the foregoing. In some aspects, the amphiphilic polymer comprises PLA-PEG. In some embodiments, PLA-PEG comprises PLA having a number-average molecular weight (MW) of 9 to 23 kg/mole, or any number range in between, e.g., 11-23, 11-21, 13-21, 13-19, 14-19, 14-18, 15-18, or 15-17 kg/mole. In other embodiments, PLA-PEG comprises PEG having a number-average MW of 0.5 to 10 kg/mole, or any number range in between, e.g., 0.5-9, 1-9, 2-9, 2-8, 3-8, 3-7, 4-7, or 4-6 kg/mole. In other aspects, the ratio of PLA and PEG (PLA:PEG) is between 1:3 to 9:1, or any number in between, e.g., 1:3-8:1, 2:5-8:1, 2:5-7:1, 1:2-7:1, 1:2-6:1, 3:5-6:1, 3:5-5:1, 2:3-5:1, 2:3-4:1, 1:1-4:1, 1:1-3:1, or 1:1-2:1. In some aspects, PLA-PEG has a weight average molecular weight of between 10-40 kg/mole, or any number range in between, e.g., 11-40, 11-38, 12-38, 12-36, 13-36, 13-34, 14-34, 14-32, 15-32, 15-30 or 18-25 kg/mole. In some embodiments, PLA-PEG is between 50% to 94.8% (weight percent) of the therapeutic NPs, e.g., 50-90%, 50-85%, 50-80%, 55-94.8%, 55-90%, 55-85%, 55-80%, 55-75%, 55-70%, or 55-65%.

Hydrophobic Short-Chain Polyester

In some embodiments, the short-chain polyester having a number-average MW of 0.5 to 8 kg/mole, or any number range in between, e.g., 0.5-7.5, 0.8-7.5, 0.8-7, 1.1-7, 1.1-6.5, 1.4-6.5, 1.4-6, 1.7-6, 1.7-5.5, 2-5.5, 2-5, 2.3-5, 2.3-4.5, 2.6-4.5, 2.6-4, or 3-4 kg/mole. Non-limiting examples of the hydrophobic short-chain polyester include, e.g., poly(3-hydroxybutyrate-co-3-hydroxyvalerate, polyethylene adipate, polybutylene succinate, polyhydroxybutyrate, polyhydroxyalkanoate, PCL, PLA, and PLGA. In some aspects, the polyester is selected from the group consisting of PCL, PLA, and PLGA. In other aspects, the polyester comprises PCL. In yet other aspects, the polyester comprises PLGA. In some embodiments, the short-chain polyester, e.g., PCL, PLA, or PLGA is between 5% and 49.8% (wt percent) of the therapeutic NPs, e.g., 5-45%, 10-45%, 10-40%, 15-45%, 15-40%, 20-45%, 20-40%, 30-45%, or 30-40%.

Amphiphilic Polymer: Hydrophobic Short-Chain Polyester Weight Ratio

In some aspects, the ratio of the weight between the amphiphilic polymer and the hydrophobic short-chain polyester (e.g., PLA-PEG:PLGA) is between 1.1 and 19, or any number in between, e.g., 1.5-19, 1.5-18, 3-18, 3-15, 4.5-15, 4.5-14, 6-14, 6-12, 7.5-12, or 7.5-10.

Temperature

In some embodiments, the NP is fabricated between 0 and 8° C., e.g., 1-8° C., 1-7° C., 2-7° C., 2-6° C., 3-6° C., 3-5° C., or 4-5° C.

NP Fabrication Using Nanoprecipitation

Polymer

Non-limiting examples of the polymer include, e.g., poly (3-hydroxybutyrate-co-3-hydroxyvalerate, polyethylene adipate, polybutylene succinate, polyhydroxybutyrate, and polyhydroxyalkanoate, PCL, PLA, and PLGA. In some aspects, the polymer is selected from the group consisting of PCL, PLA, and PLGA. In other aspects, the polymer comprises PCL. In yet other aspects, the polymer comprises PLGA. In other aspects, the polymer has a number-average MW of 20 to 70 kg/mole, or any number range in between, e.g., 22-70, 22-65, 25-65, 25-55, 28-55, 28-50, 30-50, 30-45, 32-45, or 32-42 kg/mole. In some embodiments, the polymer, e.g., PLGA is between 75% to 95.8% (weight percent) of the therapeutic NPs, e.g., 76-95%, 76-94%, 77-94%, 77-93%, 78-93%, 78-92%, 79-92%, 79-91%, 80-91%, or 80 to 89.8%.

Amphiphilic Lipid

Non-limiting examples of the amphiphilic lipid include lecithin, cholesterol, 1,2-dipalmitoyl-sn-glycero-3-phosphocholine (DPPC), dioleoyltrimethyl-ammoniumpropane (DOTAP), distearoylphosphatidylethanolamine (DSPE), rhamnolipid, phospholipids, a pegylated lipid, such as DSPE-PEG, Cholesterol-PEG, DPPC-PEG, DOTAP-PEG, DSPE-PEG, rhamnolipid-PEG, or phospholipid-PEG, and combinations thereof. In some embodiments, the amphiphilic lipid comprises lecithin having a number-average MW of 0.3 to 0.8 kg/mole, or any number range in between, e.g., 0.3-0.79, 0.4-0.79, 0.4-0.78, 0.5-0.78, 0.5-0.77, 0.6-0.77 or 0.6-0.76 kg/mole. In further embodiments, the amphiphilic lipid, e.g., lecithin, is between 4% to 24.8% (weight percent) of the therapeutic NPs, e.g., 5-24.8%, 5-24%, 6-24%, 6-23%, 7-23%, 8-23%, 8-22%, 9-22%, 9-21%, or 10-21%, 10-20%, or 10-19.8%. In other embodiments, the amphiphilic lipid comprises DSPE-PEG. In some aspects, DSPE-PEG comprises DSPE having a number-average MW of 0.3 to 0.8 kg/mole, or any number range in between, e.g., 0.3-0.79, 0.4-0.79, 0.4-0.78, 0.5-0.78, 0.5-0.77, 0.6-0.77 or 0.6-0.76 kg/mole. In other aspects, DSPE-PEG comprises PEG having a number-average MW of 1 to 5.1 kg/mole, or any number range in between, e.g., 1-4.1, 1.3-4.1, 1.3-3.1, 1.6-3.1, 1.6-2.1, or 1.9-2.1 kg/mole. In further aspects, the pegylated lipid, e.g., DSPE-PEG, is between 4% to 24.8% (wt %) of the therapeutic NPs, e.g., 5-24.8%, 5-24%, 6-24%, 6-23%, 7-23%, 8-23%, 8-22%, 9-22%, 9-21%, or 10-21%, 10-20%, or 10-19.8%. In some embodiments, the amphiphilic lipid comprises lecithin and DSPE-PEG. In other embodiments, the ratio between lecithin and DSPE-PEG is between 5% to 95% (wt %), e.g., 10-95%, 10-90%, 20-90%, 20-80%, 30-80%, 30-70%, 40-70%, 40-60%, or 45-55%. In some aspects, the ratio between lecithin and DSPE-PEG is 1:1, lecithin is between 2% to 22.8% (wt %) of the therapeutic NPs, e.g., 2-22%, 2.5-22%, 2.5-20%, 3-20%, 3-18%, 3.5-18%, 3.5-16%, 4-16%, or 5-14.8%; and DSPE-PEG is between 2% to 22.8% (wt %) of the therapeutic NPs, e.g., 2-22%, 2.5-22%, 2.5-20%, 3-20%, 3-18%, 3.5-18%, 3.5-16%, 4-16%, or 5-14.8%.

Polymer: Amphiphilic Lipid Weight Ratio

In some aspects, the ratio of the weight between the polymer and the amphiphilic lipid (e.g., PLGA:lecithin/DSPE-PEG) is between 3.3 and 24, or any number in between, e.g., 3.5-22, 4-22, 4-21, 4.5-21, 4.5-20, 5-20, 5.5-20, or 5.5-18.

Organic Solvent

In some aspects, the organic solvent is selected from the group consisting of acetonitrile, Acetone Dimethylformamide, Dimethylsulfoxide, and Tetrahydrofuran. In other aspects, the organic solvent comprises acetonitrile. In yet other aspects, the organic solvent is acetonitrile. In some embodiments, the aqueous solution was prepared by dissolving the amphiphilic lipid (e.g., lecithin and DSPE-PEG at, e.g., 7:3 molar ratio) in ethanol prior to diluting with water. In further embodiments, the final concentration of ETOH is between 2% to 10%, e.g., 2-8%, 2.2-8%, 2.2-7%, 2.4-7%, 2.4-6%, 2.6-6%, 2.6-5%, 2.8-5%, or 3-5%. In some embodiments, the dissolved polymer, e.g., PLGA, is rapidly dumped into the aqueous phase while stirring. In other embodiments, the solvent is evaporated under a stream (e.g., $N_2$ or air).

Temperature

In some embodiments, the NP is fabricated between 0 and 8° C., e.g., 1-8° C., 1-7° C., 2-7° C., 2-6° C., 3-6° C., 3-5° C., or 4-5° C.

Use of Therapeutic NPs for the Treatment of a Disorder in a Subject

In some embodiments, the active ingredient is provided in a therapeutically effective amount. As used herein, the "therapeutically effective amount" refers to any amount of the active ingredient that treats the subject, for example, a dose or a concentration that provides a therapeutically effective amount of the active ingredient (e.g., Adapalene).

The addition of a therapeutically effective amount of the active ingredient encompasses any method of dosing. In some embodiments, dosing of the active ingredient includes a single administration of the therapeutic NPs that includes the active ingredient. In other embodiments, dosing includes two, three, four, five, or six administrations of the therapeutic NPs that includes the active ingredient. In yet other embodiments, dosing includes at least seven administrations of the therapeutic NPs that includes the active ingredient. Examples include administration of the drug delivery composition for a period of time until a diminution of the disease state is achieved, preventative treatments applied before the instigation of symptoms, or any other dosing regimen known in the art or yet to be disclosed that one skilled in the art would recognize as a potentially effective regimen. A final dosing regimen including the regularity of and mode of administration depends on a number of non-limiting factors such as the subject, the severity of the affliction, the route of administration, the stage of disease development, the presence of other conditions such as pregnancy, infancy, or the presence of an additional disease; or any other factor now known or yet to be disclosed.

Determination of a therapeutically effective amount of the active ingredient is within the capability of those skilled in the art, especially in light of the detailed disclosure provided herein. The effective amount of the active ingredient and/or the drug delivery composition used to affect a particular purpose as well as its toxicity, excretion, and overall tolerance may be determined in vitro, or in vivo, by pharmaceutical and toxicological procedures either known now by those skilled in the art or by any similar method yet to be disclosed. One example is the in vitro determination of the $IC_{50}$ (half maximal inhibitory concentration) of the active ingredient in cell lines or target molecules. Another example is the in vivo determination of the $LD_{50}$ (lethal dose causing death in 50% of the tested animals) of the active ingredient. The exact techniques used in determining an effective amount will depend on factors such as the type and physical/chemical properties of the active ingredient, the property being tested, and whether the test is to be performed in vitro or in vivo. The determination of an effective amount of a particular active ingredient will be well known to one of skill in the art who will use data obtained from any tests in making that determination.

As disclosed above and herein, the drug delivery system can be used to treat a disease or condition. As used herein, treatment of a condition or disease is the practice of any method, process, or procedure with the intent of halting, inhibiting, slowing or reversing the progression of a disease, disorder or condition, substantially ameliorating clinical symptoms of a disease disorder or condition, or substantially preventing the appearance of clinical symptoms of a disease, disorder or condition, up to and including returning the diseased entity to its condition prior to the development of the disease. Generally, the effectiveness of treatment can be determined by comparing treated groups with non-treated groups.

In some aspects, the therapeutic NP is used to treat a disorder selected from the group consisting of: a central nervous system disorder, neuromuscular degeneration in the periphery, cancer, and a non-neurodegenerative-CNS disease. In some embodiments, the therapeutic NP is used for treating a neurological disorder in a subject in need thereof. In other embodiments, the therapeutic NP is used for treating a neurodegenerative disease in a subject in need thereof. In yet other embodiments, the therapeutic NP is used for treating a motor neuron disease in a subject in need thereof. In further embodiments, the therapeutic NP is used for treating ALS in a subject in need thereof. In yet further embodiments, the therapeutic NP is used for preserving motor unit in a subject in need thereof.

In certain aspects, administering the therapeutic NP (e.g., PLA-PEG/hydrophobic short-chain polyester NPs loaded with a retinoid, such as, Adapalene, or lipid-hybrid NPs loaded with a retinoid, such as, Adapalene) increases the lifespan of the subject, reduces motor impairment, reduces loss of motor neuron, reduces loss of neuromuscular junction (NMJ) innervation, reduces loss of muscle volume, reduces expression of a neuroinflammation marker (e.g., phosphorylated neurofilament heavy chain, glial fibrillary acidic protein, and Iba-1), or a combination thereof, in the subject.

The retinoid family is an intriguing therapeutic candidate for neurologic disorders [10]. Retinoic acid (RA) is a member of the retinoid family of lipids. A metabolic byproduct of Vitamin A, RA is derived in the diet from plant and animal products. In the body, Vitamin A is converted to retinol and circulates in plasma as retinol bound to retinol-binding protein-4 (RBP4) [11-12]. Retinol is taken up into cells by the interaction of RBP4 and its receptor STRA6. In the cell, retinol bound to cellular retinol-binding protein (CRBP1) are metabolized into all-trans RA (ATRA). In many cell types including neurons, RA is associated with cellular RA-binding proteins 1 and 2 (CRABP-1, CRABP-2), and its entry into the nucleus is mediated by its interaction with CRABP-2 [13].

In the nucleus, RA is bound to a transcription complex comprising ligand-activated transcription factors RA receptor (RAR) and Retinoic X Receptor (RXR). RAR has three subtypes, α, β, and γ, and multiple isoforms of each subtype generated by alternative splicing and differential promoter usage [14-15]. RARs are activated by all-trans RA (ATRA) and 9-cis-RA and regulate gene expression by heterodimerizing with RXRs. RXRs are activated only by 9-cis-RA and regulate gene expression as homodimers, heterodimerizing with RARs, or heterodimerizing with a variety of orphan receptors [16-18]. In the absence of ligand, RA nuclear receptors function as transcriptional repressors [11].

RA regulates gene transcription through RARs and RXRs [19-21]. There are 27 genes with confirmed RA response elements (RAREs). Moreover, retinoid sensitive sequences have been found in regulatory regions of more than 500 genes, including genes encoding enzymes involved in neurotransmitter biosynthesis, ligand-gated channels, and G protein-coupled receptors [10]. There is, however, little understanding of which genes would be beneficial to treat neurological disorders, and which genes potentially could accelerate pathologies.

RA signaling plays an essential role in the adult CNS, including synaptic plasticity, learning and memory, neurogenesis, and regeneration. Roles of RA signaling in the adult CNS include synaptic plasticity, learning and memory, neurogenesis, and regeneration [10]. Dysregulation of members of the RA signaling pathway has been directly linked to neurodegeneration in several diseases including AD, PD, and ALS [22-23]. For example, Vitamin A deprivation produced motor dysfunction that resembles an ALS-like phenotype and amyloid deposition that resembles an AD-like phenotype in rats [24]. Deprivation of Vitamin A or mutation of RA receptors also produces defects in spatial learning and memory [12]. RA signaling has further been implicated in the regeneration and reinnervation after peripheral nerve damage. Genes encoding enzymes that are important for RA synthesis and receptor expression are increased following nerve crush, and enhanced RA receptor expression appears to improve neurite outgrowth and neuronal regeneration [25-26]. Finally, studies in rodent models of neurodegeneration have demonstrated beneficial effects of RA or retinoid supplementation on neurodegenerative phenotypes [27-28]. Thus, retinoid signaling may be a novel therapeutic target for disorders such as motor neuron and neurodegenerative diseases.

Several lines of evidence have implicated retinoid signaling in ALS. First, expression level and distribution changes of members of the retinoid signaling pathways have been observed in postmortem tissues in animal models of ALS [13]. Second, genes of retinoid pathway proteins and genes regulated by retinoid signaling are differentially expressed in post-mortem tissues of ALS patients [29-33]. Third, in mutant SOD1 transgenic animal models of familial ALS (FALS), spinal cord gene expression profiling revealed altered expression of genes of the retinoid signaling pathway at the pre-symptomatic stage [34-35]. Fourth, dietary deprivation of vitamin A in rats leads to a loss of retinoid signaling and ALS-like phenotypes such as motor impairments, lower motor neuron loss, and inflammation within the spinal cord [24]. Finally, chronic administration of a pan RXR agonist, bexarotene (Targretin™), reduced motor impairments, increased lifespan and was neuroprotective [36]. Thus, retinoid signaling may be a therapeutic target for slowing the process of neurodegeneration and promoting regeneration of the adult nervous system in ALS [13, 27, 37-41]. For example, Jokic and colleagues observed diffuse RARα and RARβ immunostaining in lumbar spinal cord motor neurons at pre-symptomatic stages of a rat model of ALS, which declined in end-stage disease [35]. A similar decline in RARα immunoreactivity was reported in rats fed a vitamin A-deficient diet [24].

The therapeutic potential of targeting the retinoid signaling pathway, however, remains somewhat unclear. Dietary all-trans RA supplementation has been shown to accelerate ALS symptoms and significantly reduce lifespan in an ALS-mouse model [42]. Thus, indiscriminate activation of RA signaling, as opposed to targeting select receptors, may not be an appropriate ALS treatment strategy [42]. Also, previous clinical trials have demonstrated that the use of retinoids has failed to produce significant clinical benefits in AD patients [43-44].

Several lines of circumstantial evidence suggest that agonists of RARβ may be novel therapeutic targets for ALS. First, when RA signaling is altered, a specific increase of RARβ nuclear localization is detected in surviving spinal cord motor neurons of sporadic but not familial ALS patients [45]. Second, RARβ nuclear localization correlated with reduced apoptosis in the spinal cord, suggesting a neuroprotective role. Third, application of a RARβ-specific agonist, adapalene, reduced cell death following oxidative injury and excitotoxicity, suggesting a neuroprotective role against oxidative stress in primary motor neurons [45].

Adapalene is an intriguing therapeutic candidate for treating neurological diseases due to its selectivity for RARβ. It does not interact with RXRs, and $AC_{50}$ between adapalene and RARα, RARβ, and RARγ are 9.2, 2.2, and 22 nM, respectively. As a third-generation poly-aromatic retinoid, adapalene is more stable and potent than RA [46-47]. Adapalene has been shown to promote cellular differentiation and exert anti-inflammatory effects in vitro [47] and is FDA approved for the treatment of acne and cervical neoplasia. There is also in vitro evidence suggesting that adapalene may be neuroprotective against oxidative stress [45].

As used herein, the term "neurological disorder" refers to disease of the brain, spine, and the nerves that connect them. Non-limiting examples of neurological disorders include brain tumor, epilepsy, PD, stroke, frontotemporal dementia, motor neuron disease, neurodegenerative disease, neurotrauma, stroke, and neuropsychiatric illness. As used herein, the term "neurodegenerative disease" refers to conditions that result in progressive degeneration, the death of nerve cells, or both. Non-limiting examples of neurodegenerative diseases include ALS, PD, AD, HD, motor neuron disease, and Schizophrenia. As used herein, the term "motor neuron disease" refers to a group of progressive neurological disorders that destroy cells that control essential muscle activity such as speaking, walking, breathing, and swallowing. Non-limiting examples of motor neuron diseases include ALS, progressive bulbar palsy, pseudobulbar palsy, primary lateral sclerosis (PLS), progressive muscular atrophy, spinal muscular atrophy (SMA), and post-polio syndrome (PPS). As used herein, the term "motor unit" refers to a motor neuron and the skeletal muscle fibers innervated by that motor neuron's axonal terminals. As used herein, the term "preserve motor unit" comprises reducing the extent of loss in motor neuron, neuromuscular junction innervation, and muscle volume. Preserving motor unit reduces impairment in balance, muscle strength, and gait in a subject.

In some embodiments, the therapeutic NPs are used to treat cancer selected from the group consisting of acute promyelocytic leukemia, acute myeloid leukemia, estrogen receptor positive breast cancer, ovarian cancer, lung cancer, pancreative cancer, brain cancer, prostate cancer, and neuroblastoma. In further embodiments, the lung cancer comprises NSCLC. In yet further embodiments, the brain cancer is selected from the group consisting of glioblastoma and medulloblastoma.

In some aspects, the therapeutically effective amount of the therapeutic NP is administered systemically. As used herein, the term "systemic administration" refers to a route of administration of medication, nutrition or other substance into the circulatory system so that the entire body is affected. In some embodiments, the therapeutically effective amount of the therapeutic NP is administered parenterally (generally injection, infusion, or implantation). In other embodiments, the therapeutically effective amount of the therapeutic NP is administered intravenously. In yet other embodiments, the therapeutically effective amount of the therapeutic NP is administered via enteral administration (absorption of the drug through the gastrointestinal tract). In further embodiments, the therapeutically effective amount of the therapeutic NP is administered through a route selected from direct injection into the brain, injection into the intrathecal space of the spinal cord, injection into the CSF of the subarachnoid space of the brain or cerebral ventricles, intranasal injection, subcutaneous injection, and intramuscular injection.

Unless specifically noted, it is intended that the words and phrases in the specification and the claims be given their plain, ordinary, and accustomed meaning to those of ordinary skill in the applicable arts. The inventor is fully aware that he/she can be his/her own lexicographer if desired. The inventor expressly elects, as his/her own lexicographer, to use only the plain and ordinary meaning of terms in the specification and claims unless he clearly states otherwise and then further, expressly sets forth the "special" definition of that term and explains how it differs from the plain and ordinary meaning. Absent such clear statements of intent to apply a "special" definition, it is the inventor's intent and desire that the simple, plain and ordinary meaning to the terms be applied to the interpretation of the specification and claims.

The inventor is also aware of the normal precepts of English grammar. Thus, if a noun, term, or phrase is intended to be further characterized, specified, or narrowed in some way, then such noun, term, or phrase will expressly include additional adjectives, descriptive terms, or other modifiers in accordance with the normal precepts of English grammar. Absent the use of such adjectives, descriptive terms, or modifiers; it is the intent that such nouns, terms, or phrases be given their plain and ordinary English meaning to those skilled in the applicable arts.

The verb "comprise" as is used in this description and the claims and its conjugations are used in its non-limiting sense to mean that items following the word are included, but items not specifically mentioned are not excluded. Also, reference to an element by the indefinite article "a" or "an" does not exclude the possibility that more than one of the elements are present unless the context clearly requires that there is one and only one of the elements. The indefinite article "a" or "an" thus usually means "at least one."

Unless defined otherwise, technical and scientific terms used herein have the same meaning as commonly understood by one of ordinary skill in the art to which this invention belongs. Allen et al., *Remington: The Science and Practice of Pharmacy* 22$^{nd}$ ed., Pharmaceutical Press (Sep. 15, 2012); Hornyak et al., *Introduction to Nanoscience and Nanotechnology*, CRC Press (2008); Singleton and Sainsbury, *Dictionary of Microbiology and Molecular Biology* 3$^{rd}$ ed, revised ed., J. Wiley & Sons (New York, N.Y. 2006); Smith, *March's Advanced Organic Chemistry Reactions, Mechanisms and Structure* 7$^{th}$ ed., J. Wiley & Sons (New York, N.Y. 2013); Singleton, *Dictionary of DNA and Genome Technology* 3$^{rd}$ ed., Wiley-Blackwell (Nov. 28, 2012); and Green and Sambrook, *Molecular Cloning: A Laboratory Manual* 4th ed., Cold Spring Harbor Laboratory Press (Cold Spring Harbor, N.Y. 2012), provide one skilled in the art with a general guide to many of the terms used in the present application. All references cited herein are incorporated by reference in their entirety as though fully set forth.

One skilled in the art will recognize many methods and materials similar or equivalent to those described herein, which could be used in the practice of the present invention. Other features and advantages of the invention will become apparent from the following detailed description, taken in conjunction with the accompanying drawings, which illustrate, by way of example, various features of embodiments of the invention. Indeed, the present invention is in no way limited to the methods and materials described. For convenience, certain terms employed herein, in the specification, examples and appended claims are collected here.

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. Unless otherwise defined, all technical and scientific terms used herein have the same meaning as commonly understood by one of ordinary skill in the art to which this invention belongs. It should be understood that this invention is not limited to the particular methodology, protocols, and reagents, described herein and as such can vary. The definitions and terminology used herein are provided to aid in describing particular embodiments and are not intended to limit the claimed invention, because the scope of the invention is limited only by the claims.

The aspects, features, applications, and advantages will be apparent to those of ordinary skill in the art from the specification, drawings, and the claims. References are made to the figure to illustrate selected embodiments and preferred modes of carrying out the invention. It is to be understood that the invention is not hereby limited to those aspects depicted in the figure.

EXAMPLES

Having thus generally described the nature of the invention, reference will now be made to the accompanying drawings, showing by way of illustration, preferred embodiments thereof.

Example 1. Methods

Chemicals

Adapalene, acetonitrile, dichloromethane (DCM), dimethyl sulfoxide (DMSO), Dulbecco's Phosphate Buffered Saline (PBS), potassium ferricyanide, potassium ferrocyanide, sodium cholate, and sodium deoxycholate were purchased from Sigma-Aldrich (St. Louis, Mo., USA). Ester terminated poly(lactic-co-glycolic acid) (50:50; inherent viscosity=0.59 dL/g) (PLGA) was purchased from Lactel (Birmingham, Ala., USA). MPEG-P(D,L)LA (PLA-PEG) (MW: 5,000-16,000 Da) and polycaprolactone (PCL) (MW: 1,000-5,000 Da) were purchased from Akina Inc. (West Lafayette, Ind., USA). Slide-A-Lyzer Dialysis Cassettes (MWCO 5,000) was purchased from Thermo Fisher Scientific (USA).

Synthesis of Polymeric NPs with Adapalene

Poly(lactic-co-glycolic acid) (PLGA), poly(lactic acid) (PLA), poly(lactic acid)-co-poly(ethylene glycol) (PLA-PEG), and poly(caprolactone) (PCL) are members of the biocompatible aliphatic family of polyesters. These linear polymers dissolve in a variety of organic solvents and degrade in water via slow hydrolysis of ester linkages, yielding nontoxic byproducts that are readily metabolized via the Krebs cycle for elimination [48]. PLA-PEG and PLGA are biodegradable. PLGA, PLA, PLA-PEG, and PCL are approved for clinical application in various forms, including as coatings or depots [49-50]. Most importantly, drug that has been embedded in the polymer is slowly released in fluid environments, primarily via diffusion, but also as the polymer degrades and falls apart. Polyesters are excellent candidate materials to serve as biodegradable drug carriers, particularly in the form of nanoparticles, which can be suspended in water at a high concentration for injection via standard routes.

Polymeric NPs with adapalene were generated via single-emulsion-evaporation synthesis [51-52]. PLA-PEG was blended with low MW PCL (MW: 1-5 kDa) at different ratios (10, 20 or 40% PCL w/w). 50 mg of polymer (PLA-PEG:PCL ratios of 1:0, 9:1, 8:2, 6:4) and 2 mg of adapalene were dissolved in 2 ml of dichloromethane (DCM). The dissolved polymer and adapalene were added dropwise into 4 ml of a 1% w/v sodium cholate aqueous solution while rapidly vortexing and further probe sonicated on ice for three 10-second bursts at 40% amplitude. The resulting emulsion was dispersed in a 20 ml 0.3% w/v sodium cholate and gently stirred for 3 hrs to evaporate the solvent. Following solvent evaporation, the solution was passed through a 0.22 um sterile bottle top filter or centrifugal filtration to remove drug aggregates. Particles were further washed and concentrated with Amicon Ultra-15 Centrifugal filters (MWCO 100 k).

PLA-PEG was blended with low MW PLGA (MW: 1-5 kDa) at different ratios (10, 20 or 40% PLGA w/w). During the following procedure, all solvents were kept cool on ice. 240 mg of PLA-PEG and 160 mg of PLGA were dissolved in 16 ml of DCM. The polymer solution was then aliquoted into 8 glass culture tubes, and 100 μl of a 10 mg/ml solution of adapalene in DMSO were added to each glass culture tube. The dissolved polymer and adapalene solution was added dropwise into a test tube containing 4 ml of 1% w/v sodium cholate under vortex mixing then probe sonicated on ice 3×, in 10 s bursts at 40% amplitude (Fisher Scientific Model 705 Sonic Dismembrator, Waltham, Mass., USA). The formed emulsion was then transferred into a 250 ml beaker and stirred, the residual emulsion on the tube was washed out with 2 ml of 0.3% sodium cholate. The resulting polymer concentration during the evaporation step was 0.625% w/v and the drug concentration 0.0125% w/v. The solvent was allowed to evaporate for 1 h in a fume hood while under constant stirring. This step was repeated with the 7 other tubes of the polymer. 100 mg of polymer were mixed per 250 ml beaker. Large aggregates were removed by prefiltering NP solutions with 0.220 μm bottle top filters and NPs were pooled together. The NP suspension was then centrifuged in Amicon filter tubes at 5,000 RCF for 24 minutes, then NP pellet was resuspended in 9 ml of cold endotoxin-free water and centrifuged again. NPs were then resuspended, aliquoted, and stored at −80° C. until use.

Synthesis of Hybrid NPs with Adapalene

Lipid-polymer hybrid NPs were synthesized by modifying a nanoprecipitation technique [53]. 50 mg of PLGA and 2 mg of adapalene were dissolved in 10 ml of acetonitrile. A 10-ml aqueous solution was prepared by dissolving lecithin and DSPE-PEG (7:3 molar ratio) in ethanol prior to diluting with water to a final concentration of 4% EtOH and 1 mg/ml of lipid. Dissolved PLGA was rapidly dumped into the aqueous volume while stirring, and the solvent was evaporated under a stream (e.g., $N_2$ or air) for 2 hrs.

NP Characterization

Aliquots of final NP suspensions were lyophilized and massed to determine batch yield. The yield was calculated as a function of polymer output relative to polymer input. To evaluate polymer composition of blended NPs, proton nuclear magnetic resonance (H NMR) spectra were recorded of lyophilized samples dissolved in DMF (400 MHz Varian liquid state NMR, Agilent Technologies, Santa Clara, Calif., USA). Hydrodynamic radius, polydispersity index, and zeta potential were measured with a Nanobrook 90 Plus Zeta instrument (Brookhaven) on samples suspended in 1 mM KCl at a concentration of 1 mg/ml.

Adapalene Loading Quantification

Percent loading was quantified by comparing fluorescent intensity of samples dissolved in DMSO to constructed control curves. Control curves were constructed by dissolving plain particles in DMSO (1 mg/ml) and spiking 50 μl with 10 μl of a series of adapalene dilutions (final concentration range of 9-167 μg/ml). Samples were plated on black flat-bottom 96 well plates in triplicate. Furthermore, all samples were acidified by adding 10 μl of 10 mM HCl. Fluorescent intensities were measured at excitation/emission wavelengths of 360/420 nm, determined by excitation/emission scans resulting in the greatest fluorescent intensity on a Tecan microplate reader. Percent drug loading is determined by a ratio between adapalene that is not lost in the aqueous phase during fabrication and adapalene that was initially added to the polymer phase.

Controlled Release of Adapalene

Adapalene release profiles were evaluated by dialyzing NPs against 2 L of 1×PBS at 37° C. All NP formulations were diluted to an Adapalene concentration of 0.1 mg/ml, and 400 μl were added to Slide-A-Lyzer Dialysis Cassettes with an MWCO of 3,500 Da. At pre-determined time points (0, 1, 2, 4, 6, 24, 48, 72, 144, 168 hr), 10 μl was removed from dialysis cassettes, dissolved in 190 μl of DMSO, and 50 μl was plated in triplicate on a black flat-bottom 96-well plate. Fluorescent intensities of sample time points were measured on a Tecan plate reader (see adapalene quantification) to determine the quantity of adapalene remaining in the NPs at each time point.

NP Treatment of Mice $SOD1^{G93A}$ transgenic mice began treatment with Adap-NPs at 61 days of age, injected with a dosage of 3 mg/kg of adapalene encapsulated within NPs via the lateral tail vein, 3 times a week. Adap-Ctl mice were injected with equivalent amounts of blank nanoparticles.

Assessing the Biological Activity of Adap-NPs In Vivo

Mice were monitored for health until endpoints when mice could not right themselves after 15 seconds, were reached.

Bioactivity of adapalene-loaded NPs in the central nervous system was evaluated in transgenic mice expressing a β-galactosidase reporter gene under the control of the retinoic acid responsive element (RARE) (Jackson Laboratories, stock #008477). 2.5 mg/kg Adapalene loaded NPs were intravenously administered via lateral tail vein to 4 to 6 week-old mice. 2.5 mg/kg NPs without Adapalene were intravenously administered via lateral tail vein to 4 to 6-week-old control mice. Mice were sacrificed 4 hours later, n=3 per group.

At 4 or 24 h post-administration, mice were anesthetized and perfused with heparinized saline. Tissues were postfixed in 4% PFA (48 h at 4° C.) and then cryopreserved in 30% sucrose (48 h at 4° C.). Tissues were frozen and cryosectioned to a thickness of 16 μm and mounted on charge microscope glass slides. β-galactosidase expression was evaluated by X-gal staining of tissue sections. Sections were washed in a 2 mM $MgCl_2$, 0.01% sodium deoxycholate staining buffer for 10 minutes at room temperature while rocking. Sections were transferred to a staining solution composed of staining buffer supplemented with 1 mg/ml X-Gal, 5 mM potassium ferricyanide, and 5 mM potassium ferrocyanide, and incubated overnight at 37° C. Slides were then washed with 1×PBS and mounted with gelvatol and a glass cover slip. Slides were imaged on an Olympus BX40 light microscope.

For Western blot analysis, tissue extractions were prepared by homogenizing spinal cords in RIPA buffer with protease and phosphatase inhibitors using a bead homogenizer. Tissue extractions were then centrifuged at 12,000 g for 15 minutes, and supernatants were collected. RARE activation was probed using a β-galactosidase antibody.

Behavioral Assays

After 9 weeks of treatment, mice were analyzed by the open-field test and their muscle strength and balance were quantified by measuring the number of rearing episodes during an 8-minute trial. After 12 weeks of treatment, gait analysis, such as hind and fore-limb stride length, and stance, were performed using the foot-print measurements.

Example 2. Effects of Temperature and NP Composition on Loading and Releasing of Adapalene Our initial efforts to produce NPs via standard techniques produced particles very poorly loaded with adapalene possessed a highly negative surface charge that would be unsuitable for in vivo delivery and surprisingly high batch variability.

Figure 1:
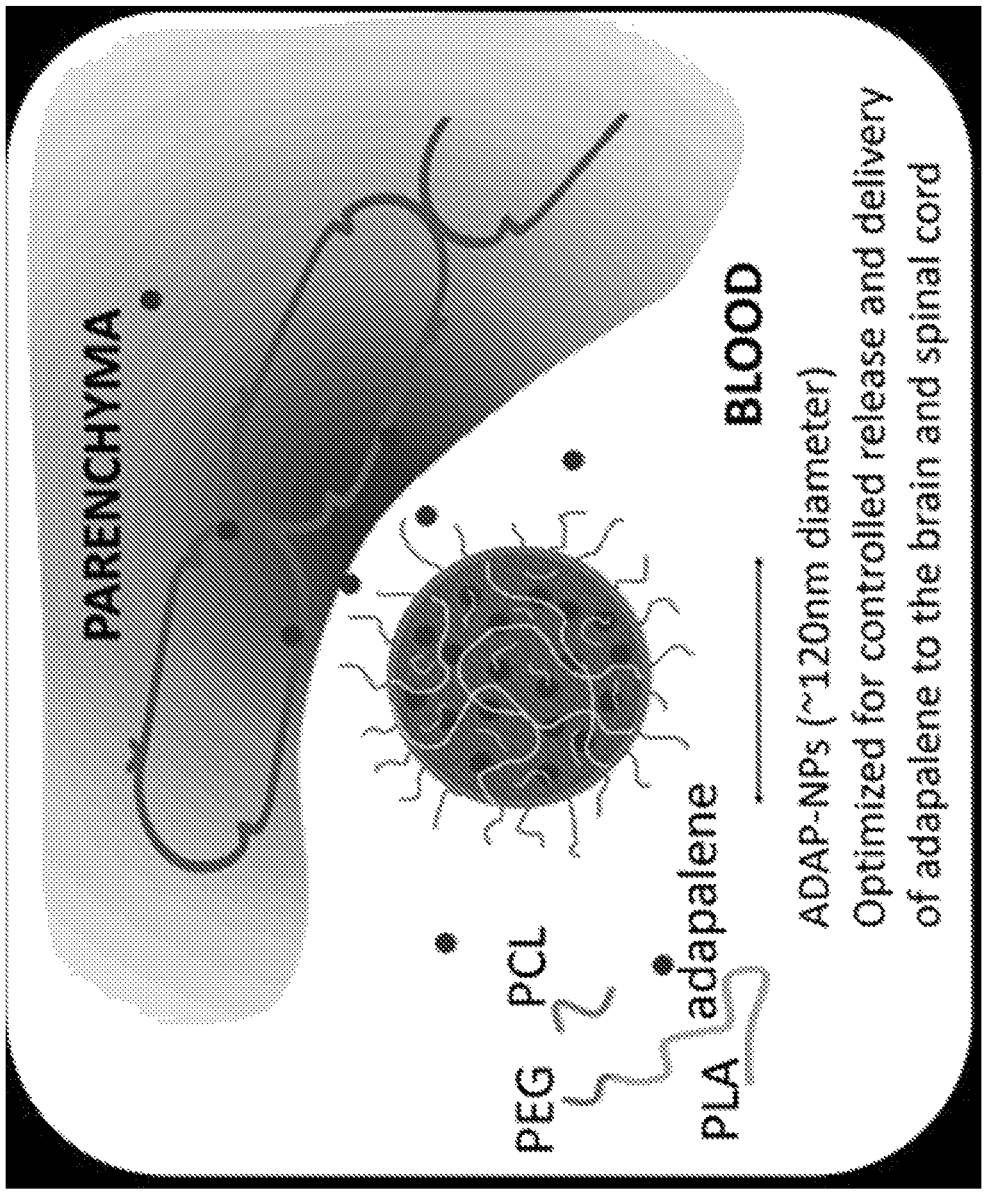
FIG. 1. ADAP-Polymer-Based NPs PLA-PEG is blended with low MW PCL to generate NPs highly loaded with adapalene, which is released from the NPs in physiological environments.
Figure 2:
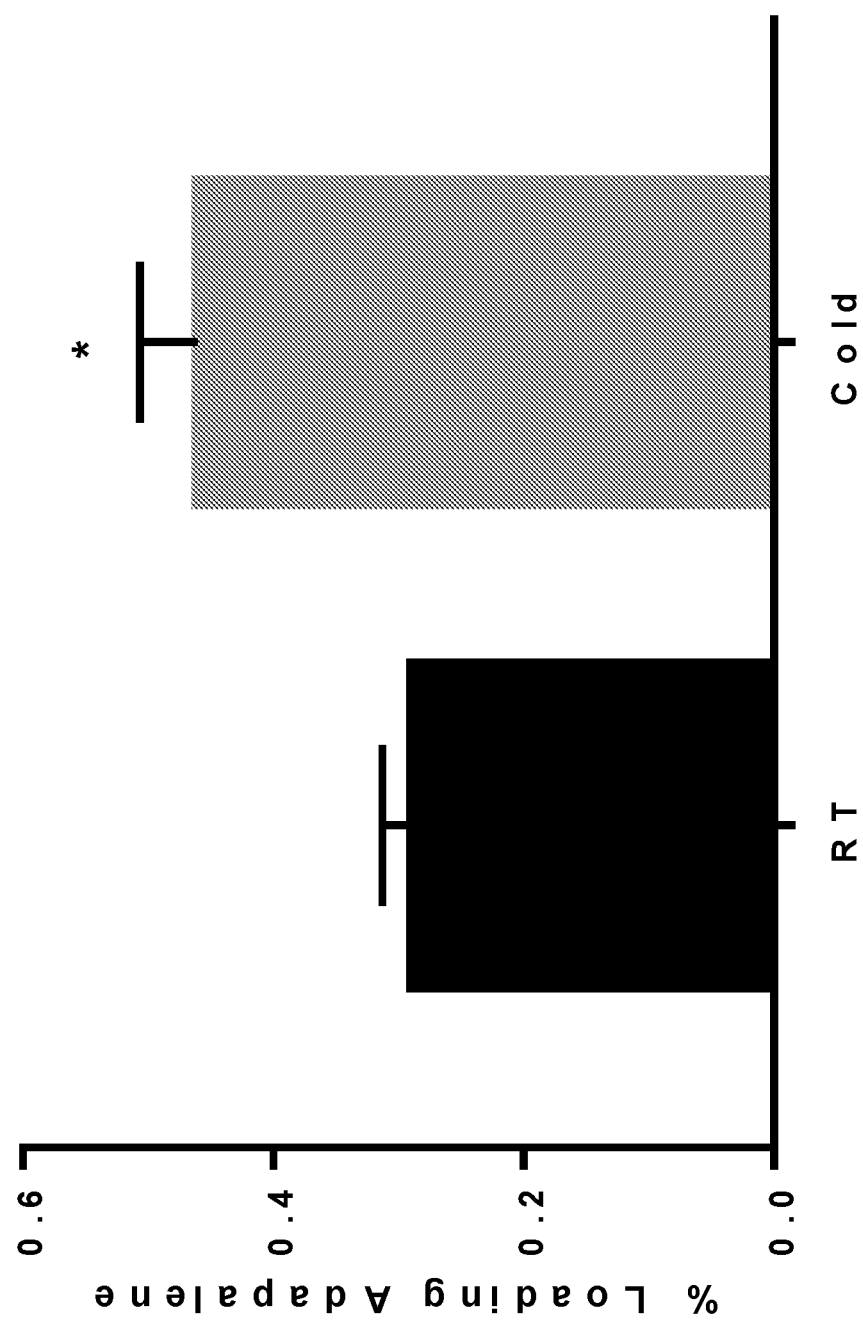
FIG. 2. Effect of Emulsion Temperature on Adapalene Loading Loading measurement revealed that maintaining a lower temperature significantly increased adapalene loading into PLA-PEG NPs.

We found that temperature significantly impacts Adapalene loading. NPs were formulated either with cold solutions on ice or at room temperature (RT). Temperatures of mixing, evaporation, and subsequent washing were controlled. We observed that maintaining a cold temperature (4° C.) improved loading by 80% percent over room temperature preparations, which was statistically significant (FIG. 2).

Figure 3:
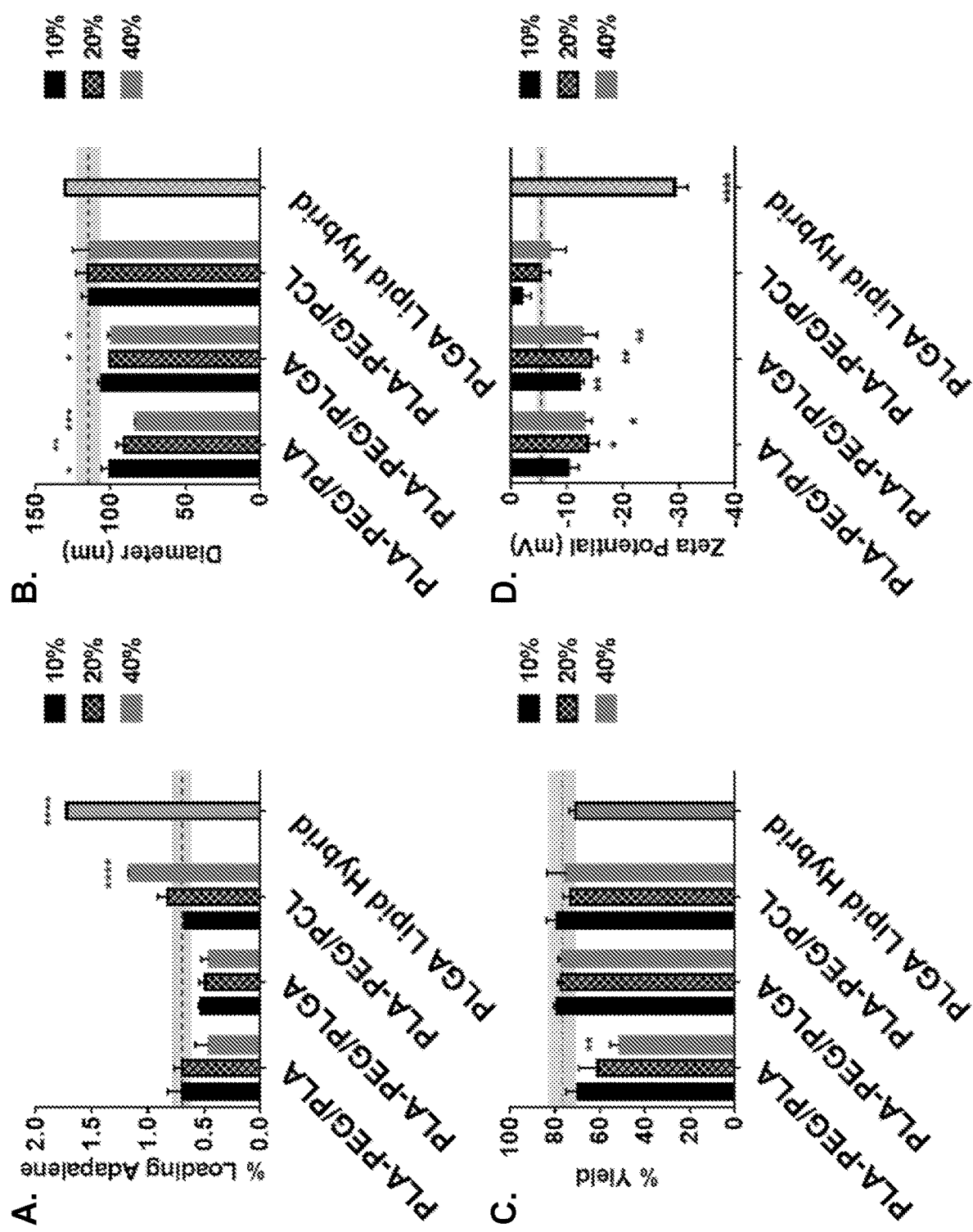
FIG. 3. Optimizing the Design of ADAP-NPs Multiple formulations of blended NPs were engineered to encapsulate adapalene. Dashed lines represent "initial" (non-optimized) formulation (PLA-PEG), which was poorly loaded and had a very negative surface charge. (A) The highest loading was achieved using hybrid NPs. Of the blended formulations, the highest loading was achieved by blending a PLA-PEG base with 40% w/w short-chain PCL. (B)-(D) This approach maintained a desirable NP diameter (B), good yield (C), and zeta potential (D).

We found that NP composition also significantly impacts adapalene encapsulation. We modified the polymer blending methods [54] for the formation of nanoparticles via emulsion. Blending low MW PLA into the PLA-PEG base (10, 20, or 40 PLA wt %) did not improve loading but decreased average diameter, zeta potential, and percent yield as a function of how much PLA was added (FIG. 3). Blending low MW PCL into the PLA-PEG base (10, 20, or 40 PCL wt %) significantly improved the loading (0.70% to 1.17% with 40 wt % PCL in PLA-PEG) (FIG. 3A). Addition of PCL did not affect diameter, surface charge, or percent yield relative to non-blended PLA-PEG controls (FIG. 3B-D). We also modified the lipid hybrid methods [55] for the formation of NPs via emulsion. Blending DSPE-PEG into a PLGA base produced lipid-polymer hybrid NPs. The hybrid approach produced the highest encapsulation out of any method tested (1.92%). However, these NPs were also characterized by a highly negative surface charge (−31.77 mV).

DLS measurements of the hydrodynamic diameter revealed there were no significant differences between blank NPs (103.65±3.93 nm) and adapalene loaded NPs (Adap-NPs) (105.79±5.43 nm). Adapalene loading within NPs was relatively consistent at an average of 1.0±0.03% w/w and encapsulation efficiency of 39.4±1.25%.

Figure 4:
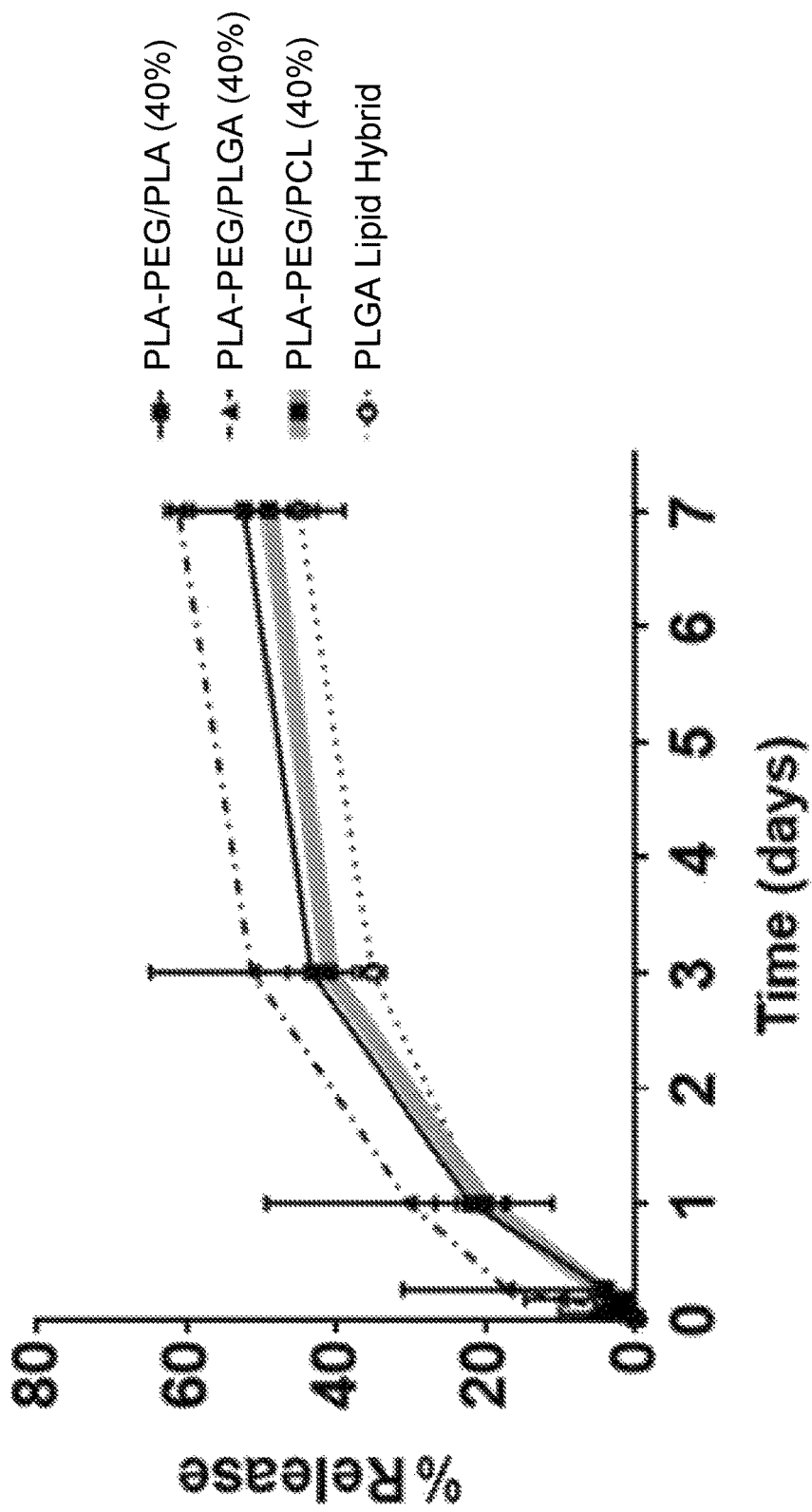
FIG. 4. Adapalene is slowly released into buffered saline at 37° C. Hybrid NPs exhibited slower release of adapalene.
Figure 5:
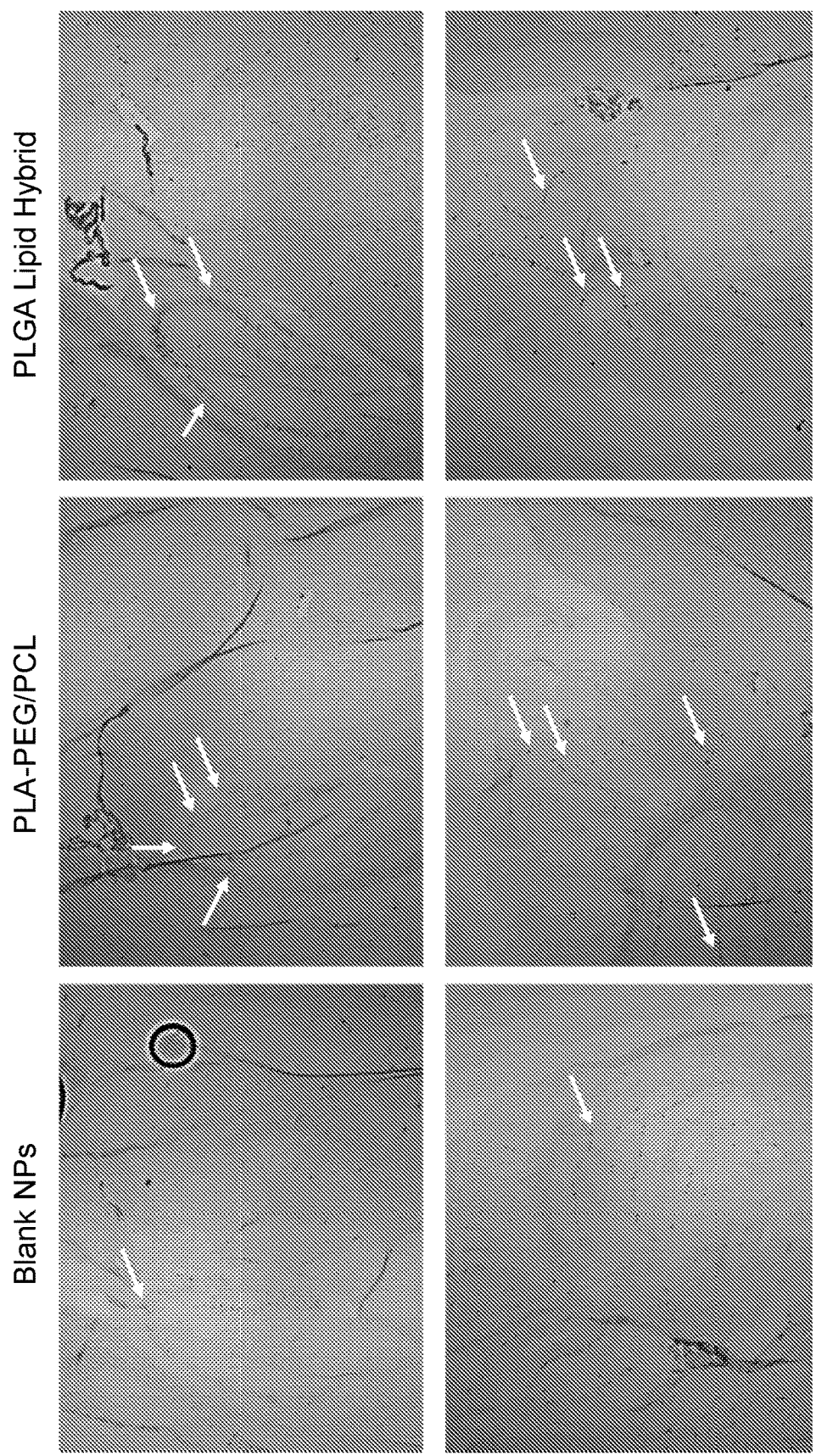
FIG. 5. In vivo activity of adapalene loaded NPs. Four hours post administration, hybrid NPs produced the highest retinoid signaling in vivo.

To test whether different encapsulation strategies altered the release of adapalene from NPs, each formulation was incubated in PBS at 37° C. and sampled at regular intervals. No significant differences in adapalene release were observed for any formulation compared to PLA-PEG control. Approximately 20% of adapalene was released after 24 hours, and complete release was not observed even after 7 days (FIG. 4).

In sum, manipulating solvent composition and emulsion temperature enabled us to generate NPs with higher loading and favorable surface (~0.6% w/w, "Base" formulation). Blending low MW polyesters into the base formulation to produce a more hydrophobic core enabled us to reach a loading of nearly 10-fold higher over our initial formulation (1.2% w/w). These optimized NPs maintained high yield (80%), a good size (117 nm), and a good surface charge (close to neutral), which confer desirable circulation properties [56]. This highly loaded design enables us to activate retinoid signaling in the CNS without needing to manipulate the BBB or BSCB or engineer drug or drug carrier for transport across the BBB or BSCB.

Example 3. The Bioactivity of Adapalene Loaded NPs

ADAP-NPs are highly loaded with bioactive adapalene. Once incubated in aqueous media, ADAP-NPs slowly release their payload over several days (FIG. 4). In both primary motor neuron and NSC-43 cell cultures, NP encapsulated adapalene retains equivalent potency to free drug and is neuroprotective.

Example 4. The Bioactivity of Systemically Delivered Retinoid Adapalene Loaded NP In Vivo When injected directly into the striatum of healthy mice, Adap-NPs and free adapalene equivalently activated MAPK signaling. In vivo testing used either the 40% PCL-blended or the lipid hybrid NPs. Treatments of Adap-NP were well tolerated, and no adverse reactions were observed. Two hours after Adap-NPs were administered i.v. to healthy mice at a dose of 5 mg/kg, we measured Adapalene at a concentration of 1.9±0.29 μM in whole brain homogenate. This concentration was within the range of neuroprotective effects observed in cell culture.

Figure 6:
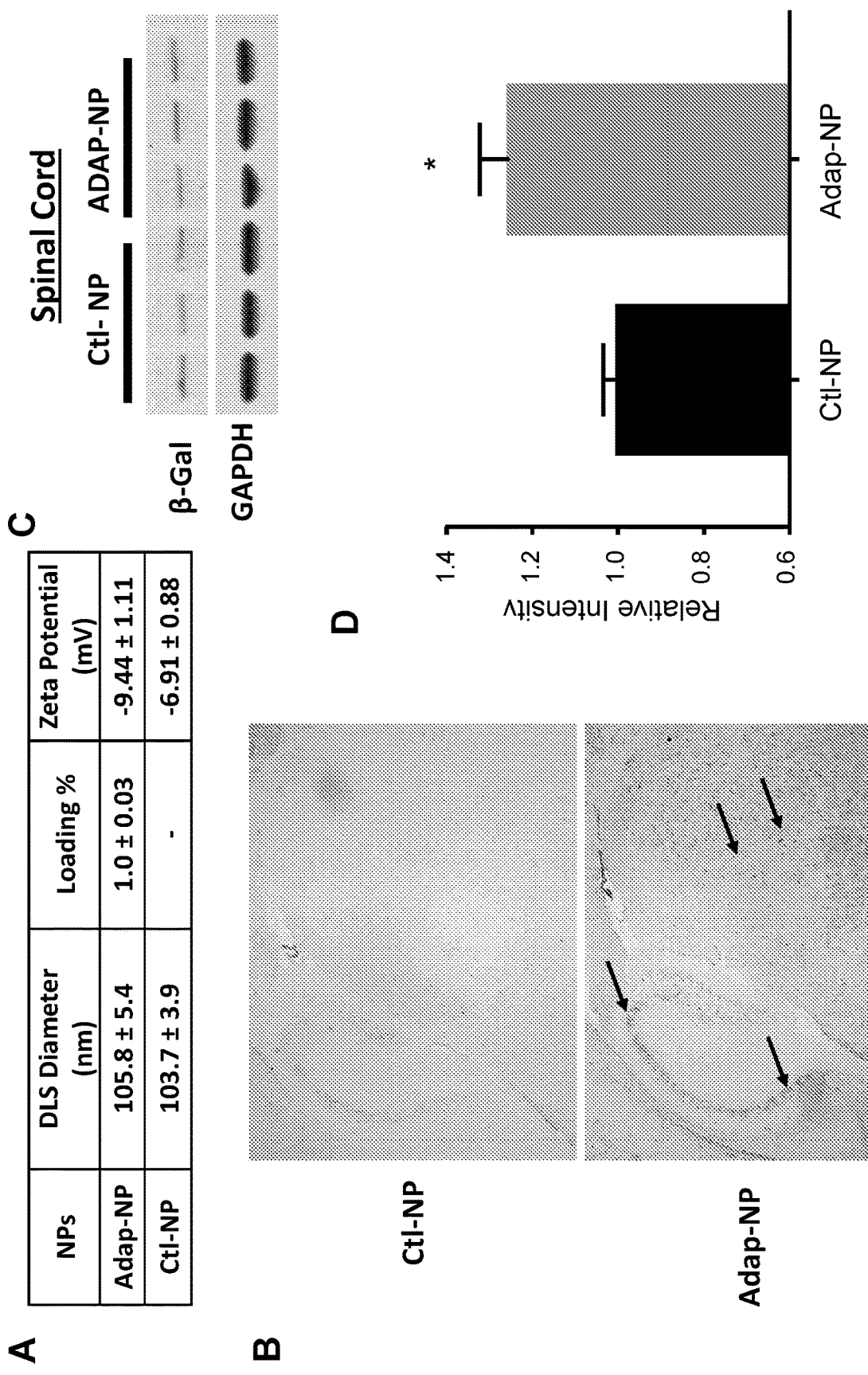
FIG. 6. Biophysical Characterization & Biological Activity of Adapalene-Loaded NPs (Adap-NP) (A) Biophysical characteristics of Adap-NP (PLA-PEG/PLGA (40%)) (B) Peripheral Adap-NP administration induced retinoid signaling in the brain. Retinoid signaling reporter (RARE) mice were sacrificed 24 hr after 2.5 mg/kg of Adap-NP administration and stained with X-gal to image the lacZ reporter gene expression in the brain. (C)-(D) Adap-NP administration increased retinoid signaling in the spinal cord. Western blot and quantification of β-galactosidase from lysates of the spinal cord in reporter mice. Controls represent RARE mice injected with the drug-empty NP. There is no difference between RARE mice that received saline versus drug-empty NP injections.
Figure 7:
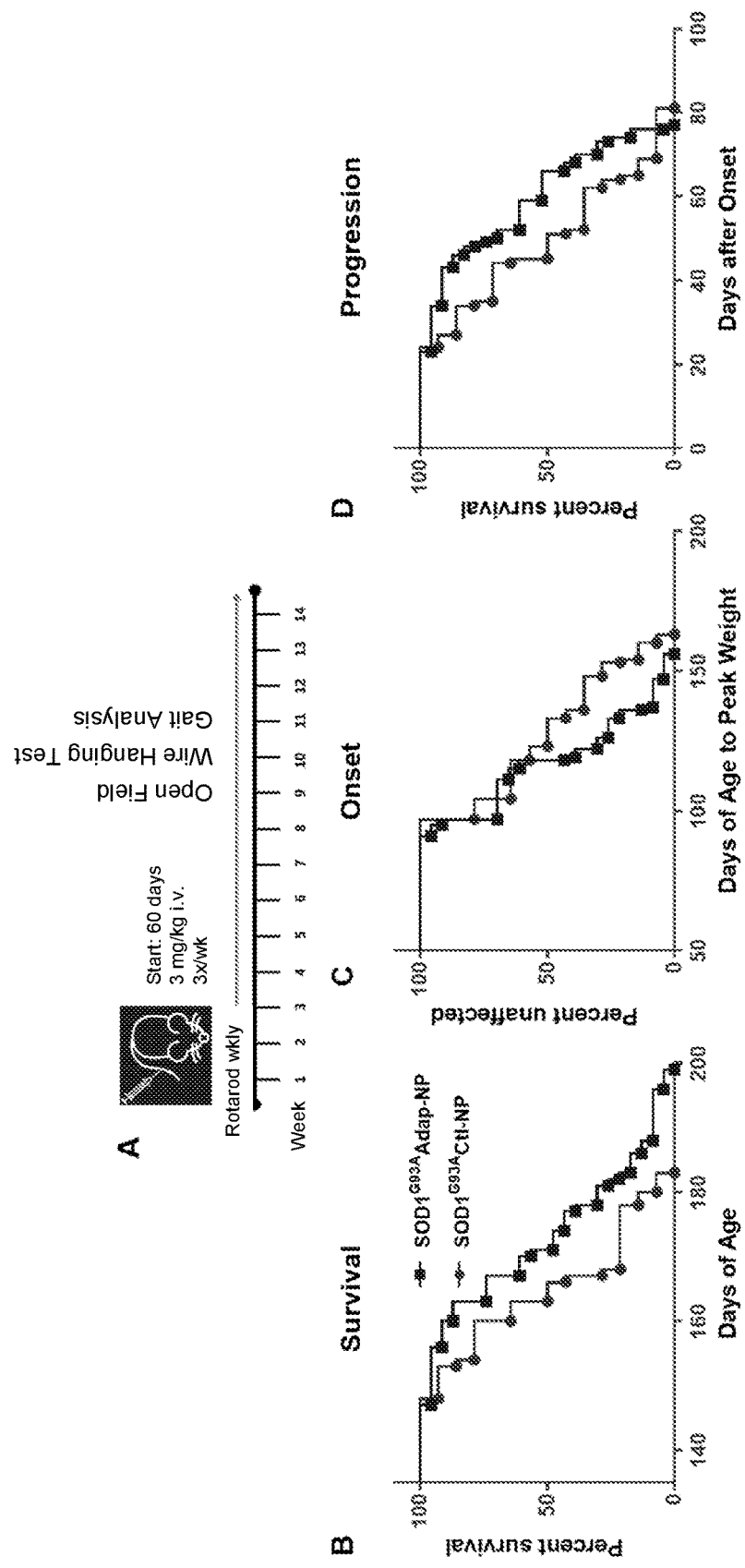
FIG. 7. Treatment with Adap-NPs significantly increases lifespan by slowing disease progression in $SOD1^{G93A}$ mice. (A) Schematic detailing of NP administration and behavioral assay schedule (B) Lifespan (days): average: Ctl-NP=164.5; Adap-NP=171 (Gehan-Breslow-Wilcoxon test, p=0.03); max: Ctl-NP=183; Adap-NP=199. (C) Kaplan-Meier plot representing the days of age to onset (peak weight) (D)

Staining with X-gal to visualize lacZ expression demonstrated that systemic Adap-NP administration could induce retinoid signaling throughout the CNS including in the cerebellum, cortex, and striatum. Four hours after Adap-NPs were administered to transgenic mice bearing a LacZ reporter for the RA response element (RARE), robust activation of retinoid signaling across the central nervous system was observed (FIG. 6). The level of activation positively correlated with the dose. Wide-spread activation was found throughout the CNS, including the striatum and cerebellum, areas that have been previously shown to express high levels of RARβ [15]. The highest levels of activation were observed in the hippocampus, Purkinje cells of the cerebellum, and spinal cord. Mice that received injections of vehicle (PLA-PEG NPs lacking adapalene) showed low levels of reporter gene expression throughout the brain, including the hippocampus and cerebellum. Interestingly, Adapalene delivered with PCL NPs did not show a noticeable increase in β-galactosidase activity compared to blank particles.

Administration of Adap-NPs also increased the expression of lacz transgene in the spinal cord, the part of the CNS which is classically affected in ALS disease progression. Western blot analysis of Adap-NPs treated mice showed increase β-galactosidase expression in the spinal cord (FIG. 6). Thus, systemic delivery of the retinoid adapalene, e.g., using intravenous administration of Adap-NPs, activate retinoid signaling in the brain and spinal cord.

In sum, treatment with adapalene loaded hybrid NPs was able to elicit a biological response as quickly as 4 hours post injection in reporter mice. This is the first evidence to demonstrate that polymeric NPs can deliver adapalene to the CNS.

Example 5. Chronic Systemic Administration of Adapalene Loaded NPs Increases Extends Lifespan in SOD1$^{G93A}$ Mice Chronic systemic administration was initiated in SOD1$^{G93A}$ mice at 61 days of age and consisted of 3× weekly injections of NPs lacking drug or 3 mg/kg of Adapalene (encapsulated within Adap-NPs); wild-type subjects served as positive control for all assays.

To test whether chronic systemic administration of Adap-NPs would be neuroprotective in context of disease, we utilized the SOD1$^{G93A}$ transgenic murine model of ALS. The SOD1$^{G93A}$ transgenic line recapitulates key features of ALS in humans [57-65] and is the most common preclinical model for ALS translational studies. Superoxide dismutase 1 (SOD1) is a Cu, Zn metalloprotein located in the cytoplasm, where it acts as a free-radical scavenger to catalyze the dismutation of $O_2$— into oxygen and hydrogen peroxide. Mutations in SOD1 are found in 10-20% of patients with familial ALS and 3% of patients with sporadic ALS [50]. The G93A transgenic mouse possesses a Gly93Ala substitution that results in a progressive and ultimately fatal motor neuron degeneration. Transgenic SOD1$^{G93A}$ mice provide a robust, reproducible, and biologically relevant model of the progression of ALS pathology. Previously, considerable variance in the onset and duration of clinical signs of motor system illness can be observed in transgenic mice on a genetically heterogeneous background (C57BL/6J×SJL/J). A broad range of survival due to genetic background modifiers and litter and gender effects requires large cohorts of mice to obtain reliable test results [66-67]. To minimize genetic variation, the laboratory of Dr. Greg Cox has developed a congenic strain of the SOD1G93A transgene on an inbred C57BL/6J background at The Jackson Laboratory (JR #004435). The B6.Cg-Tg(SOD1*$^{G93A}$)1Gur/J strain shows a consistent phenotype with no gender differences in either disease onset or lifespan. Two independent studies were published that showed a combined male and female median lifespan of 161±10 days (n=140) and 157±9 days (n=45), respectively, demonstrating the robustness of the model [67-68].

Survival of SOD1$^{G93A}$ transgenic mice was prolonged by chronic systemic administration of Adap-NPs. The average lifespan of transgenic mice treated with control nanoparticles was 164 days, compared to 171 days for transgenic mice that were treated with Adap-NPs (FIG. N2B; p=0.03 Gehan-Breslow-Wilcoxon test). Also, the max lifespan of transgenic mice was extended from 183 days for the group control group to 199 days for mice on Adap-NPs. Thus, chronic administration of Adap-NPs produced significant prolongation of lifespan in SOD1$^{G93A}$ mice, increasing median survival and maximum lifespan by 7 and 16 days, respectively.

Interestingly, mice treated with control NPs reached their maximum weight (128 days) 7 days after than mice treated with ADAP-NPs (135 days) (FIG. 8). Of note, wild-type mice treated Adap-NPs appeared to gain weight at a slightly slower rate, and the differences become more apparent at approximately 120 days, which is also when transgenic mice begin to decline in weight precipitously. It is possible that beneficial effects of Adap-NPs on weight loss in SOD1$^{G93A}$ transgenic might be masked by reduced weight gain compared to mice treated with control NPs. In sum, the results suggest that polymeric particles can be used to deliver adapalene systemically to activate RARβ for therapeutic purposes.

Example 6. Chronic Systemic Administration of Adapalene Loaded NPs Reduces Motor Impairment in SOD1$^{G93A}$ Transgenic Mice Chronic Adap-NP administration significantly decreases impairment in balance, muscle strength, and gait in the SOD1$^{G93A}$ transgenic mice. The effects of Adap-NP treatment on motor performance were analyzed using the accelerating rotarod test. After the initiation of NP treatment, mice were subjected to weekly accelerating rotarod testing with 3 trials per week. In the first rotarod session, the motor performance of SOD1$^{G93A}$ transgenic mice was impaired compared to wild-type mice. Adap-NP treatment showed no significant differences in rotarod performance at these early time points in wild-type or transgenic mice. As the treatment progressed, compared to transgenic mice treated with control NPs, transgenic mice treated with Adap-NPs displayed a slower rate of decline in rotarod performance (FIG. 9A). At the 12$^{th}$ week of treatment, Adap-NP treated mice averaged 71.42±6.00 sec compared to control treated mice which averaged 60.12±5.46 sec, which was a decline in performance compared to week 1 baseline of 71.42±6.00% and 60.12±5.46% (p=0.02), respectively. Likewise, at week 13, Adap-NP treated mice averaged 65.23±5.46 sec compared to control treated mice which averaged 43.35±6.82 sec, which was a decline in performance compared to week 1 baseline of 54.39±8.39% and 90.00±12.34% (p=0.03), respectively (FIG. 9A). Week 14 also demonstrated decreased decline in Adap-NP treated mice compared to control, but did not reach significance (p=0.08) (FIG. 9A).

The effects of Adap-NP treatment on muscle strength and balance were analyzed using the open-field test. After 9 weeks of treatment, the number of rearing episodes during an 8-minute trial were quantified. While Adap-NPs did not produce significant changes in wild-type mice, transgenic mice treated with Adap-NPs had significantly more rearing episodes with an average of 26.76±1.41 compared to transgenic mice on control NPs, 16.83±1.29 (FIG. 9B, p<0.001).

The effects of Adap-NP treatment on muscle strength were also analyzed using the wire hanging test after 10 weeks of treatment. Mice were allowed to suspend from a thin wire using forelimbs and hind limbs, and their average performance over 3 trials was measured. Again, SOD1$^{G93A}$ transgenic mice treated with Adap-NP were able to hang longer with an average time of 29.04±3.84 secs compared to transgenic mice with an average of 18.70±2.60 secs (p=0.03) (FIG. 9C).

Gait analysis was performed after 12 weeks of treatment using the foot-print measurements. Features of gait including hind and fore-limb stride length and stance were measured. Compared to wild-type mice, SOD1$^{G93A}$ transgenic mice treated with control NPs showed significant decreases in the different gait measures (FIG. 9D). However, Adap-NP treatment significantly reduced gait impairments in transgenic mice (FIG. 9D, stride p<0.01; stance p<0.02). Together, these behavioral tests demonstrate that chronic Adap-NP administration significantly improves motor function and/or decreases impairment of balance, muscle strength, and gait in the SOD1$^{G93A}$ transgenic mice.

Example 7. Chronic Systemic Administration of Adapalene Loaded NPs Preserves Motor Units and Confers Neuroprotective Effects in SOD1$^{G93A}$ Transgenic Mice To determine the potential mechanisms underlying effects of Adap-NPs in extending lifespan and improvement in motor performance, we investigated effects of chronic systemic administration of Adapalene loaded NPs on maintenance of spinal motor neurons, neuromuscular junction innervation, and muscle volume. Mice from each group (n=3-4) were euthanized at 104 or 143 days of age, representing early or late stages of the disease, respectively. Motor neuron were labeled using ChAT immunofluorescence and quantified within the ventral horn of lumbar spinal cord.

Chronic systemic administration of Adapalene loaded NPs improves maintenance of spinal motor neurons. The number of motor neurons progressively decreased in transgenic mice compared to wild-type mice (FIG. 10A). At 104 days of age, transgenic mice treated with Adap-NP had an average of 17.7±0.64 motor neurons per section compared to 15.0±0.5 motor neurons per section for transgenic on control NPs (p=0.024) (FIG. 10A). At 143 days of age, transgenic mice treated with Adap-NP had 15.1±0.82 motor neurons per section compared to 11.45±1.05 motor neurons per section for transgenic mice on control NPs (p=0.027) (FIG. 10A). Thus, treatment with Adap-NPs significantly reduced the extent of motor neuron loss at both early and late stages of the ALS, demonstrating the neuroprotective effect of treatment in the spinal cord.

Chronic systemic administration of Adapalene-loaded NPs preserves gastrocnemius neuromuscular junction integrity. Loss of colocalization of neurofilament and bungarotoxin was used as a measure of denervation. Compared to WT mice, neuromuscular junction innervation significantly decreased between 104 and 143 days of age in transgenic mice. However, transgenic mice that were treated with Adap-NPs had significantly more innervated neuromuscular junctions. At 104 days, 72.15±2.59% neuromuscular junctions were innervated in transgenic mice treated with Adap-NPs, compared to 63.61±6.11% in control-treated transgenic mice (p=0.08) (FIG. 11A). At 143 days of age, transgenic mice that were treated with Adap-NPs had significantly more innervated neuromuscular junctions at an average of 56.38±7.79% compared to 40.03±2.34% in control-treated mice (p<0.01) (FIG. 11A).

Chronic systemic administration of Adapalene loaded NPs also reduces muscle loss. Muscle fiber diameter from the gastrocnemius muscle was measured to determine the effects of Adap-NP treatment on muscle loss (FIG. 11B). On day 104, there were no significant differences between transgenic mice in either treatments group. Averaged muscle diameters are 24±1.00 μm and 25.33±0.88 μm for the control and Adap-NP group, respectively. However, at day 143, the average muscle fiber diameter was significantly reduced in transgenic mice that were treated with control, with an average diameter of 19±1.25 μm. In contrast, mice that were treated with Adap-NPs had an observed diameter of 24.33±0.67 μm (p=0.04) (FIG. 11B).

Motor neuron loss was reduced by roughly 50% in the Adap-NP treated groups at early and late time points of ALS, suggesting reduced disease progression. More motor neurons in the lumbar spinal cord also correlated with more neuromuscular innervation of the gastrocnemius muscle. Thus, chronic systemic administration of adapalene-loaded NPs not only maintains cell bodies in the spinal cord but also preserves functional synapses with muscle fibers and maintains the size of muscle fibers.

Example 8. Chronic Systemic Administration of Adapalene-Loaded NPs Reduces Neuroinflammation Markers in the Spinal Cords of SOD1$^{G93A}$ Transgenic Mice A major hallmark of ALS, neuroinflammation, was decreased following chronic treatment with Adap-NPs. Neuroinflammation increases with age in SOD1$^{G93A}$ transgenic mice. Using GFAP as a marker for astrogliosis, we found that treatment with Adap-NPs significantly reduced immunoreactivity in the lumbar spinal cords of transgenic mice compared to controls (FIG. 12). Also, using Iba-1 staining to assess for microgliosis, we found that immunoreactivity was reduced in transgenic mice following Adap-NP treatment compared to control mice. These findings are in agreement with previous reports that retinoic acid can decrease inflammation and that specific agonism of RARβ can reduce neuroinflammation [26, 36, 69].

REFERENCES

1. Cudkowicz, M., M. Qureshi, and J. Shefner, Measures and markers in amyotrophic lateral sclerosis. NeuroRx, 2004. 1(2): p. 273-83.
2. Tapia, R., Cellular and molecular mechanisms of motor neuron death in amyotrophic lateral sclerosis: a perspective. Front Cell Neurosci, 2014. 8: p. 241.
3. Bruijn, L. I., T. M. Miller, and D. W. Cleveland, Unraveling the mechanisms involved in motor neuron degeneration in ALS. Annu Rev Neurosci, 2004. 27: p. 723-49.
4. Writing, G. and A. L. S. S. G. Edaravone, Safety and efficacy of edaravone in well defined patients with amyotrophic lateral sclerosis: a randomised, double-blind, placebo-controlled trial. Lancet Neurol, 2017. July; 16(7): 505-12.
5. Pardridge, W. M., The blood-brain barrier: Bottleneck in brain drug development. NeuroRx, 2005. 2(1): p. 3-14.
6. Schinkel, A. H., P-Glycoprotein, a gatekeeper in the blood-brain barrier. Advanced drug delivery reviews, 1999. 36(2-3): p. 179-194.
7. Ballabh, P., A. Braun, and M. Nedergaard, The blood-brain barrier: An overview: Structure, regulation, and clinical implications. Neurobiology of Disease, 2004. 16(1): p. 1-13.

8. Waterhouse, R. N., Determination of lipophilicity and its use as a predictor of blood-brain barrier penetration of molecular imaging agents. Mol Imaging Biol, 2003. 5(6): p. 376-89.
9. Alavijeh, M. S., et al., Drug metabolism and pharmacokinetics, the blood-brain barrier, and central nervous system drug discovery. NeuroRx, 2005. 2(4): p. 554-71.
10. Lane M A, Bailey S J (2005) Role of retinoid signalling in the adult brain. Prog Neurobiol 75:275-93.
11. Mey J, McCaffery P. Retinoic acid signaling in the nervous system of adult vertebrates. Neuroscientist. 2004 October; 10(5): 409-21.
12. Maden M. Retinoic acid in the development, regeneration and maintenance of the nervous system. Nat Rev Neurosci. 2007 October; 8(10): 755-65.
13. Malaspina A, Michael-Titus A T. Is the modulation of retinoid and retinoid-associated signaling a future therapeutic strategy in neurological trauma and neurodegeneration? J Neurochem. 2008 February; 104(3): 584-95.
14. Arfaoui A, Lobo M V, Boulbaroud S, Ouichou A, Mesfioui A, Arenas M I. Expression of retinoic acid receptors and retinoid X receptors in normal and vitamin A deficient adult rat brain. Ann Anat. 2013 March; 195(2): 111-21.
15. Krezel W, Kastner P, Chambon P. Differential expression of retinoid receptors in the adult mouse central nervous system. Neuroscience. 1999; 89(4): 1291-300.
16. Mangelsdorf, D. J. and R. M. Evans, The RXR heterodimers and orphan receptors. Cell, 1995. 83(6): p. 841-50.
17. Kastner, P., Chambon, P., and Leid, M., Role of nuclear retinoic acid receptors in the regulation of gene expression, in Vitamin A in Health and Disease, R. Blomhoff, Editor. 1994, Marcel Dekker Inc.: New York. p. 189-238
18. Kliewer, S. A., Umesono, K., Evans, R. M. and Mangelsdorf, D. J., The retinoid X receptors: modulators of multiple hormonal signalling pathways, in Vitamin A in Health and Disease, R. Blomhoff, Editor. 1994, Marcel Dekker Inc.: New York. p. 239-55.
19. Chambon P. A decade of molecular biology of retinoic acid receptors. FASEB J. 1996 July; 10(9): 940-54.
20. Leid, M., P. Kastner, and P. Chambon, Multiplicity generates diversity in the retinoic acid signalling pathways. Trends Biochem Sci, 1992. 17(10): p. 427-33.
21. Jonk, L. J., et al., Isolation and developmental expression of retinoic-acid-induced genes. Dev Biol, 1994. 161(2): p. 604-14.
22. Malaspina A, Turkheimer F. A review of the functional role and of the expression profile of retinoid signaling and of nuclear receptors in human spinal cord. Brain Res Bull. 2007 Mar. 15; 71(5): 437-46.
23. Shudo K, Fukasawa H, Nakagomi M, Yamagata N. Towards retinoid therapy for Alzheimer's disease. Curr Alzheimer Res. 2009 June; 6(3): 302-11.
24. Corcoran J, So P L, Maden M. Absence of retinoids can induce motoneuron disease in the adult rat and a retinoid defect is present in motoneuron disease patients. J Cell Sci. 2002 Dec. 15; 115(Pt 24): 4735-41.
25. Yip P K, Wong L F, Pattinson D, Battaglia A, Grist J, Bradbury E J, Maden M, McMahon S B, Mazarakis N D. Lentiviral vector expressing retinoic acid receptor beta2 promotes recovery of function after corticospinal tract injury in the adult rat spinal cord. Hum Mol Genet. 2006 Nov. 1; 15(21): 3107-18.
26. Goncalves M B, Malmqvist T, Clarke E, Hubens C J, Grist J, Hobbs C, Trigo D, Risling M, Angeria M, Damberg P, Carlstedt T P, Corcoran J P. Neuronal RARβ Signaling Modulates PTEN Activity Directly in Neurons and via Exosome Transfer in Astrocytes to Prevent Glial Scar Formation and Induce Spinal Cord Regeneration. J Neurosci. 2015 Nov. 25; 35(47): 15731-45.
27. Riancho J. Retinoids and PPAR agonists: Promising partners in neurodegenerative diseases? Free Radic Biol Med. 2016 August; 97:616-617.
28. Esteves M, Cristóvão A C, Saraiva T, Rocha S M, Baltazar G, Ferreira L, Bernardino L. Retinoic acid-loaded polymeric nanoparticles induce neuroprotection in a mouse model for Parkinson's disease. Front Aging Neurosci. 2015 Mar. 6; 7:20.
29. Malaspina, A., N. Kaushik, and J. de Belleroche, A 14-3-3 mRNA is up-regulated in amyotrophic lateral sclerosis spinal cord. J Neurochem, 2000. 75(6): p. 2511-20.
30. Malaspina, A., N. Kaushik, and J. de Belleroche, Differential expression of 14 genes in amyotrophic lateral sclerosis spinal cord detected using gridded cDNA arrays. J Neurochem, 2001. 77(1): p. 132-45.
31. Malaspina, A. and J. de Belleroche, Spinal cord molecular profiling provides a better understanding of amyotrophic lateral sclerosis pathogenesis. Brain Res Brain Res Rev, 2004. 45(3): p. 213-29.
32. Jiang, Y. M., et al., Gene expression profile of spinal motor neurons in sporadic amyotrophic lateral sclerosis. Ann Neurol, 2005. 57(2): p. 236-51.
33. Dangond, F., et al., Molecular signature of late-stage human ALS revealed by expression profiling of postmortem spinal cord gray matter. Physiol Genomics, 2004. 16(2): p. 229-39.
34. Yoshihara, T., et al., Differential expression of inflammation- and apoptosis-related genes in spinal cords of a mutant SOD1 transgenic mouse model of familial amyotrophic lateral sclerosis. J Neurochem, 2002. 80(1): p. 158-67.
35. Jokic, N., et al., Retinoid receptors in chronic degeneration of the spinal cord: observations in a rat model of amyotrophic lateral sclerosis. J Neurochem, 2007. 103(5): p. 1821-33.
36. Riancho J, Ruiz-Soto M, Berciano M T, Berciano J, Lafarga M. Neuroprotective Effect of Bexarotene in the SOD1(G93A) Mouse Model of Amyotrophic Lateral Sclerosis. Front Cell Neurosci. 2015 Jul. 1; 9: 250.
37. Wong, L. F., et al., Retinoic acid receptor beta2 promotes functional regeneration of sensory axons in the spinal cord. Nat Neurosci, 2006. 9(2): p. 243-50.
38. Harvey, B. K., et al., Midkine and retinoic acid reduce cerebral infarction induced by middle cerebral artery ligation in rats. Neurosci Lett, 2004. 369(2): p. 138-41.
39. Corcoran, J., et al., Retinoic acid receptor beta2 and neurite outgrowth in the adult mouse spinal cord in vitro. J Cell Sci, 2002. 115(Pt 19): p. 3779-86.
40. Corcoran, J. P., P. L. So, and M. Maden, Disruption of the retinoid signalling pathway causes a deposition of amyloid beta in the adult rat brain. Eur J Neurosci, 2004. 20(4): p. 896-902.
41. Craft, N. E., et al., Carotenoid, tocopherol, and retinol concentrations in elderly human brain. J Nut Health Aging, 2004. 8(3): p. 156-62.
42. Crochemore C, Virgili M, Bonamassa B, Canistro D, Pena-Altamira E, Paolini M, Contestabile A. Long-term dietary administration of valproic acid does not affect, while retinoic acid decreases, the lifespan of G93A mice, a model for amyotrophic lateral sclerosis. Muscle Nerve. 2009 April; 39(4): 548-52.
43. Levine T D, Bowser R, Hank N C, Gately S, Stephan D, Saperstein D S, Van Keuren-Jensen K. A Pilot Trial of Pioglitazone HCl and Tretinoin in ALS: Cerebrospinal Fluid Biomarkers to Monitor Drug Efficacy and Predict Rate of Disease Progression. Neurology Research International (2012): 582075. Neurol Res Int Available at: https://www.hindawicom/journals/nri/2012/582075/ref/ [Accessed May 15, 2018].
44. Cummings J L, Zhong K, Kinney J W, Heaney C, Moll-Tudla J, Joshi A, Pontecorvo M, Devous M, Tang A, Bena J (2016) Double-blind, placebo-controlled, proof-of-concept trial of bexarotene in moderate Alzheimer's disease. Alzheimers Res Ther 8:4.
45. Kolarcik C L, Bowser R. Retinoid signaling alterations in amyotrophic lateral sclerosis. Am J Neurodegener Dis. 2012; 1(2): 130-45.
46. Shroot B, Michel S. Pharmacology and chemistry of adapalene. J Am Acad Dermatol. 1997 June; 36(6 Pt 2):S96-103.
47. Michel S, Jomard A, Démarchez M. Pharmacology of adapalene. Br J Dermatol. 1998 October; 139 Suppl 52:3-7.
48. Lu, J. M., Wang X, Marin-Muller C, Wang H, Lin P H, Yao Q, Chen C., Current advances in research and clinical applications of PLGA-based nanotechnology. Expert Review of Molecular Diagnostics, 2009. 9(4): p. 325-41.
49. Kapoor, D. N., et al., PLGA: a unique polymer for drug delivery. Ther Deliv, 2015. 6(1): p. 41-58.
50. Makadia, H. K. and S. J. Siegel, Poly Lactic-co-Glycolic Acid (PLGA) as Biodegradable Controlled Drug Delivery Carrier. Polymers (Basel), 2011. 3(3): p. 1377-97.
51. Cook R L, Householder K T, Chung E P, Prakapenka A V, DiPerna D M, Sirianni R W. A critical evaluation of drug delivery from ligand modified nanoparticles: Confounding small molecule distribution and efficacy in the central nervous system. J Control Release. 2015 Dec. 28; 220(Pt A): 89-97.
52. Householder K T, DiPerna D M, Chung E P, Wohlleb G M, Dhruv H D, Berens M E, Sirianni R W. Intravenous delivery of camptothecin-loaded PLGA nanoparticles for the treatment of intracranial glioma. Int J Pharm. 2015 Feb. 20; 479(2): 374-80.
53. Lu, J. M., Wang X, Marin-Muller C, Wang H, Lin P H, Yao Q, Chen C., Current advances in research and clinical applications of PLGA-based nanotechnology. Expert Review of Molecular Diagnostics, 2009. 9(4): p. 325-41.
54. Govender T, Stolnik S, Garnett M C, Ilium L, Davis S S. PLGA nanoparticles prepared by nanoprecipitation: drug loading and release studies of a water soluble drug. J Control Release. 1999 Feb. 1; 57(2): 171-85.
55. Chan J M, Zhang L, Yuet K P, Liao G, Rhee J W, Langer R, Farokhzad O C. PLGA-lecithin-PEG core-shell nanoparticles for controlled drug delivery. Biomaterials. 2009 March; 30(8): 1627-34.
56. Gref R, Luck M, Quellec P, Marchand M, Dellacherie E, Harnisch S, Blunk T, Müller R H. 'Stealth' corona-core nanoparticles surface modified by polyethylene glycol (PEG): influences of the corona (PEG chain length and surface density) and of the core composition on phagocytic uptake and plasma protein adsorption. Colloids Surf B Biointerfaces, 2000. 18(3-4): p. 301-13.
57. Deng H X, Hentati A, Tainer J A, Iqbal Z, Cayabyab A, Hung W Y, Getzoff E D, Hu P, Herzfeldt B, Roos R P, et al., Amyotrophic lateral sclerosis and structural defects in Cu,Zn superoxide dismutase. Science, 1993. 261(5124): p. 1047-51.
58. Gurney M E, Pu H, Chiu A Y, Dal Canto M C, Polchow C Y, Alexander D D, Caliendo J, Hentati A, Kwon Y W, Deng H X, et al., Motor neuron degeneration in mice that express a human Cu,Zn superoxide dismutase mutation. Science, 1994. 264 (5166): p. 1772-74.
59. Rosen, D. R., Mutations in Cu/Zn superoxide dismutase gene are associated with familial amyotrophic lateral sclerosis. Nature, 1993. 362(6415): p. 59-62.
60. Tu P H, Raju P, Robinson K A, Gurney M E, Trojanowski J Q, Lee V M., Transgenic mice carrying a human mutant superoxide dismutase transgene develop neuronal cytoskeletal pathology resembling human amyotrophic lateral sclerosis lesions. Proc Natl Acad Sci USA. 1996 Apr. 2; 93(7):3155-60.
61. Ferraiuolo L, Heath P R, Holden H, Kasher P, Kirby J, Shaw P J., Microarray analysis of the cellular pathways involved in the adaptation to and progression of motor neuron injury in the SOD1 G93A mouse model of familial ALS. J Neurosci., 2007. 27(34): p. 9201-19.
62. Hensley K, Floyd R A, Gordon B, Mou S, Pye Q N, Stewart C, West M, Williamson K., Temporal patterns of cytokine and apoptosis-related gene expression in spinal cords of the G93A-SOD1 mouse model of amyotrophic lateral sclerosis. J Neurochem, 2002. 82(2): p. 365-74.
63. Olsen M K, Roberds S L, Ellerbrock B R, Fleck T J, McKinley D K, Gurney M E., Disease mechanisms revealed by transcription profiling in SOD1-G93A transgenic mouse spinal cord. Ann Neurol., 2001. 50(6): p. 730-40.
64. Perluigi M, Fai Poon H, Hensley K, Pierce W M, Klein J B, Calabrese V, De Marco C, Butterfield D A., Proteomic analysis of 4-hydroxy-2-nonenal-modified proteins in G93A-SOD1 transgenic mice—A model of familial amyotrophic lateral sclerosis. Free Radic Biol Med., 2005. 38(7): p. 960-68.
65. Zhang B, Tu P, Abtahian F, Trojanowski J Q, Lee V M., Neurofilaments and orthograde transport are reduced in ventral root axons of transgenic mice that express human SOD1 with a G93A mutation. Journal of Cell Biology, 1997. 139(5): p. 1307-15.
66. Scott S, Kranz J E, Cole J, Lincecum J M, Thompson K, Kelly N, Bostrom A, Theodoss J, Al-Nakhala B M, Vieira F G, Ramasubbu J, Heywood J A., Design, power, and interpretation of studies in the standard murine model of ALS. Amyotroph Lateral Scler., 2008. 9(1): p. 4-15.
67. Heiman-Patterson T D, Sher R B, Blankenhorn E A, Alexander G, Deitch J S, Kunst C B, Maragakis N, Cox G., Effect of genetic background on phenotype variability in transgenic mouse models of amyotrophic lateral sclerosis: a window of opportunity in the search for genetic modifiers. Amyotroph Lateral Scler., 2011. 12(2): p. 79-86.
68. Wooley C M, Sher R B, Kale A, Frankel W N, Cox G A, Seburn K L., Gait analysis detects early changes in transgenic SOD1(G93A) mice. Muscle Nerve. 20, 2005. 32(1): p. 43-50.
69. Wang R, Chen S, Liu Y, Diao S, Xue Y, You X, Park E A, Liao F-F, All-trans retinoic acid reduces BACE1 expression under inflammatory conditions via modulation of NFκB signaling, J Biol Chem:jbc. 2015. M115.662908.

What is claimed is:
1. A therapeutic nanoparticle, comprising:
   a. a poly(lactic) acid-poly(ethylene)glycol (PLA-PEG) copolymer comprising PLA having a number-average molecular weight of 9-23 kg/mole, and PEG having a number-average molecular weight of 0.5-10 kg/mole;
   b. a polymer, wherein the polymer is a short-chain polyester having a number-average molecular weight of 0.5-8 kg/mole; and c. a biologically active ingredient, wherein the zeta potential of the nanoparticle is between −50 and 20 mV.

2. The nanoparticle of claim 1, wherein the polymer is selected from the group consisting of polycaprolactone (PCL), PLA, poly(lactic-co-glycolic acid) (PLGA), poly(glycolic-acid) (PGA), poly (lactide-co-caprolactone), polyethylene adipate, polybutylene succinate, polyhydroxybutyrate, polyhydroxyalkanoate, poly(3-hydroxybutyrate-co-3-hydroxyvalerate), and combinations thereof.

3. The nanoparticle of claim 2, wherein the polymer is selected from the group consisting of PCL, PLA, and PLGA.

4. The nanoparticle of claim 3, wherein the polymer comprises PLGA.

5. A therapeutic nanoparticle, comprising:
  a. a poly(lactic) acid-poly(ethylene)glycol (PLA-PEG) copolymer comprising PLA having a number-average molecular weight of 9-23 kg/mole, and PEG having a number-average molecular weight of 0.5-10 kg/mole;
  b. a polymer, wherein the polymer is a short-chain polyester having a number-average molecular weight of 0.5-8 kg/mole; and
  c. a biologically active ingredient, wherein the active ingredient has a partition coefficient (log P) of 2-10.

6. The nanoparticle of claim 1, wherein the weight percent of the active ingredient is between 0.2 to 5.

7. A therapeutic nanoparticle, comprising:
  a. a poly(lactic) acid-poly(ethylene)glycol (PLA-PEG) copolymer comprising PLA having a number-average molecular weight of 9-23 kg/mole, and PEG having a number-average molecular weight of 0.5-10 kg/mole;
  b. a polymer, wherein the polymer is a short-chain polyester having a number-average molecular weight of 0.5-8 kg/mole; and
  c. a biologically active ingredient, wherein the active ingredient comprises a retinoid.

8. The nanoparticle of claim 7, wherein the retinoid is selected from the group consisting of adapalene, retinoic acid, BMS 753, AM 80, EC19, CD1530, AM 580, TTNB, Ch 55, BS 961, AC 55649, AC261066, BMS 543, EC 23, Fenretinide, Isotretinoin, and Tazarotene.

9. The nanoparticle of claim 7, wherein the retinoid comprises adapalene.

10. The nanoparticle of claim 1, wherein the PLA-PEG has a weight average molecular weight of 10 to 40 kg/mol.

11. A therapeutic nanoparticle, comprising:
  a. a poly(lactic) acid-poly(ethylene)glycol (PLA-PEG) copolymer comprising PLA having a number-average molecular weight of 15-17 kg/mole, PEG has a number-average molecular weight of 4-6 kg/mole;
  b. a polymer, wherein the polymer is a short-chain polyester having, and the short chain polyester has a number-average molecular weight of 2-5 kg/mole; and
  c. a biologically active ingredient.

12. The nanoparticle of claim 1, wherein the weight percent of PLA-PEG is between 50 to 94.8, and the weight percent of the short-chain polyester is between 5 to 49.8.

13. The nanoparticle of claim 5, wherein the polymer is selected from the group consisting of polycaprolactone (PCL), PLA, poly(lactic-co-glycolic acid) (PLGA), poly(glycolic-acid) (PGA), poly (lactide-co-caprolactone), polyethylene adipate, polybutylene succinate, polyhydroxybutyrate, polyhydroxyalkanoate, poly(3-hydroxybutyrate-co-3-hydroxyvalerate), and combinations thereof.

14. The nanoparticle of claim 7, wherein the polymer is selected from the group consisting of polycaprolactone (PCL), PLA, poly(lactic-co-glycolic acid) (PLGA), poly(glycolic-acid) (PGA), poly (lactide-co-caprolactone), polyethylene adipate, polybutylene succinate, polyhydroxybutyrate, polyhydroxyalkanoate, poly(3-hydroxybutyrate-co-3-hydroxyvalerate), and combinations thereof.

15. The nanoparticle of claim 1, wherein the active ingredient comprises a retinoid.

16. The nanoparticle of claim 1, wherein the active ingredient has a partition coefficient (log P) of 2-10.

17. The nanoparticle of claim 7, wherein the active ingredient has a partition coefficient (log P) of 2-10.

18. The nanoparticle of claim 1, wherein the hydrodynamic diameter of the nanoparticle is between 50 and 300 nm.

19. The nanoparticle of claim 7, wherein the hydrodynamic diameter of the nanoparticle is between 50 and 300 nm.

20. The nanoparticle of claim 11, wherein the hydrodynamic diameter of the nanoparticle is between 50 and 300 nm.

* * * * *

UNITED STATES PATENT AND TRADEMARK OFFICE
CERTIFICATE OF CORRECTION

| | |
|---|---|
| PATENT NO. | : 11,446,267 B2 |
| APPLICATION NO. | : 16/616222 |
| DATED | : September 20, 2022 |
| INVENTOR(S) | : Rachael Sirianni, David Alexandro Medina and Eugene Chung |

It is certified that error appears in the above-identified patent and that said Letters Patent is hereby corrected as shown below:

In the Claims

Claim 11, Column 32, Line 7, "a short-chain polyester having, and the short chain polyester has a number-average" should read --a short-chain polyester having a number-average--.

Signed and Sealed this
Seventh Day of May, 2024

Katherine Kelly Vidal
*Director of the United States Patent and Trademark Office*